US006287572B1

(12) United States Patent
Kingsman et al.

(10) Patent No.: US 6,287,572 B1
(45) Date of Patent: Sep. 11, 2001

(54) ANTI-HIV PEPTIDES AND PROTEINS

(75) Inventors: Alan J. Kingsman; Susan M. Kingsman, both of Oxon (GB); Paula M. Cannon, Los Angeles, CA (US)

(73) Assignee: Oxford Biomedica (UK) Limited, Oxford (GB)

( * ) Notice: Subject to any disclaimer, the term of this patent is extended or adjusted under 35 U.S.C. 154(b) by 0 days.

(21) Appl. No.: 09/367,953

(22) PCT Filed: Feb. 23, 1998

(86) PCT No.: PCT/GB98/00563

§ 371 Date: Aug. 24, 1999

§ 102(e) Date: Aug. 24, 1999

(87) PCT Pub. No.: WO98/37089

PCT Pub. Date: Aug. 27, 1998

(30) Foreign Application Priority Data

Feb. 24, 1997 (GB) .................................................. 9703802

(51) Int. Cl.$^7$ .......................... A61K 34/21; A61K 39/00; A61K 39/38; A61K 39/12; A61K 38/00
(52) U.S. Cl. ..................................... 424/208.1; 424/184.1; 424/185.1; 424/186.1; 424/187.1; 424/204.1; 424/205.1; 530/300; 530/326
(58) Field of Search .............................. 424/184.1, 185.1, 424/186.1, 188.1, 204.1, 205.1, 208.1; 530/300, 326

(56) References Cited

U.S. PATENT DOCUMENTS 5,612,453  *  3/1997   Niedrig et al. ........................ 530/327

FOREIGN PATENT DOCUMENTS

| 0 334301 | 9/1989 | (EP) . |
| 0 490 383 | 6/1992 | (EP) . |
| WO 96 37623 | 11/1996 | (WO) . |

OTHER PUBLICATIONS

Niedrig et al.; Inhibition of infectious human immunodeficiency virus . . . ; J. Gen. Vir.; 75; pp. 1469–1474, 1994.*
Massiah et al; Three–dimensional structure of the human immunodeficiency virus . . . ; J. Mol. Vir.; 244; pp. 198–223, 1994.*

Neidrig, "Inhibition of infectious human immunodeficiency Virus type 1 particle formation Gag prote–derived peptides", *Journal of General Virology*, vol. 75, 1994, pp. 1469–1474.

Matthews et al, "Refined solution structure of p17, the HIV matrix protein" *Biochemical Society Transactions*, vol. 23, No. 4, Nov. 1995, pp. 725–729.

Massiah et al, "Three–dimensional structure of the Human Immunodeficiency Virus type 1 matrix protein" *Journal of Molecular Biology*, vol. 244, No. 2, 1994, pp. 198–223.

Cannon et al, "Murine Leukemia Virus–based tat–inducible Long Terminal Repeat repalcement vectors: a new system for anti–Human Immunodeficiency Virus gene therapy", *Journal of Virology*, vol. 70, No. 11, Nov. 1996, pp. 8234–8240.

Matthews et al, "Structural similarity between the p17 matrix protein of HIV–1 and interferon", *Nature*, vol. 370, No. 6491, Aug. 25 1994, pp. 666–668.

Cornelissen et al,"Human Immunideficiency Virus type 1 subtypes defined by env show high frequency of recombinant gag genes", *Journal of Virology*, vol 70, No. 11, Nov. 1996, pp. 8209–8212.

Cannon et al, "Structure–function studies of the Human Immunodeficiency Virus type 1 matrix protein p17", *Journal of Virology*, vol. 71, No. 5, May 1997, pp. 3474–3483.

* cited by examiner

*Primary Examiner*—Brett L. Nelson
(74) *Attorney, Agent, or Firm*—Nixon & Vanderhye P.C.

(57) ABSTRACT

This invention relates to novel peptides and proteins and nucleic acids encoding them, which are useful against HIV infection. The peptides comprise an amino acid sequence of a part of the HIV-1 p17 protein or of the HIV-2 p16 protein, from amino acid residues 31 to 45 or from amino acid residues 41 to 55. The proteins are recombinant p16 and p17 proteins having an alteration in helix A which is defined by amino acid residues 31 to 46, or the A-B loop which is defined by amino acid residues 47 to 52.

4 Claims, 5 Drawing Sheets

Fig.1.

Sequence encoding p17

ATG GGT GCG AGA GCG TCA GTA TTA AGC GGG

GGA GAA TTA GAT CGA TGG GAA AAA ATT CGG

TTA AGG CCA GGG GGA AAG AAA AAA TAT AAA

TTA AAA CAT ATA GTA TGG GCA AGC AGG GAG

CTA GAA CGA TTC GCA GTT AAT CCT GGC CTG

<u>TTA GAA ACA TCA GAA GGC TGT AGA CAA ATA</u>

CTG GGA CAG CTA CAA CCA TCC CTT CAG ACA

GGA TCA GAA GAA CTT AGA TCA TTA TAT AAT

ACA GTA GCA ACC CTC TAT TGT GTG CAT CAA

AGG ATA GAG ATA AAA GAC ACC AAG GAA GCT

TTA GAC AAG ATA GAG GAA GAG CAA AAC AAA

AGT AAG AAA AAA GCA CAG CAA GCA GCA GCT

GAC ACA GGA CAC AGC AGC CAG GTC AGC CAA

AAT TAC

Peptide 1 coding sequence is in bold type
Peptide 2 coding sequence is underlined p17 AMINO ACID SEQUENCE

```
                                                        PEPTIDE 1...
MGARASVLSG   GELDRWEKIR   LRPGGKKKYK   LKHIVWASRE
LERFAVNPGL   LETSEGCRQI   LGQLQPSLQT   GSEELRSLYN
    PEPTIDE 2
TVATLYCVHQ   RIEIKDTKEA   LDKIEEEQNK   SKKKAQQAAA
DTGHSSQVSQ   NY
```

Fig.4.

5NCHUBIP SEQUENCE [SEQ ID NO: 12]

```
         SalI
**GTCGACGC CGGCCAAGAC AGCACAGACA GATTGACCTA
  -------------------------- 1
TTGGGGTGTT TCGCGAGTGT GAGAGGGAAG CGCCGCGGCC

TGTATTTCTA GACCTGCCCT TCGCCTGGTT CGTGGCGCCT

TGTGACCCCG GGCCCCTGCC GCCTGCAAGT CGAAATTGCG

CTGTGCTCCT GTGCTACGGC CTGTGGCTGG ACTGCCTGCT
                                    _____
GCTGCCCAAC TGGAGCGTCC ATGG
------------------------- 2          NcoI
```

Sequences contained in PCR primers 1 (SEQ ID NO: 13) and 2 (SEQ ID NO:14) are underlined.

```
                         SEQUENCE LISTING

<160> NUMBER OF SEQ ID NOS: 131

<210> SEQ ID NO 1
<211> LENGTH: 15
<212> TYPE: PRT
<213> ORGANISM: Human immunodeficiency virus

<400> SEQUENCE: 1

Leu Lys His Ile Val Trp Ala Ser Arg Glu Leu Glu Arg Phe Ala
  1               5                  10                  15

<210> SEQ ID NO 2
<211> LENGTH: 15
<212> TYPE: PRT
<213> ORGANISM: Human immunodeficiency virus

<400> SEQUENCE: 2

Leu Glu Arg Phe Ala Val Asn Pro Gly Leu Leu Glu Thr Ser Glu
  1               5                  10                  15

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
atgttaaaac atatagtatg ggcaagcagg gagctagaac gattctgata a           51

<210> SEQ ID NO 4
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
atgctagaac gattcgcagt taatcctggc ctgttagaaa catcatgata a           51

<210> SEQ ID NO 5
<211> LENGTH: 89
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
ccggatccgg aattcgtcga ccatgttaaa acatatagta tgggcaagca gggagctaga     60
acgattctga taaagatctg gaattccgg                                       89
```

```
<210> SEQ ID NO 6
<211> LENGTH: 90
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
ccgggaattc agatctgtcg accatgctag aacgattcgc agttaatcct ggcctgttag     60
aaacatcatg ataaggatcc ggaattccgg                                      90

<210> SEQ ID NO 7
<211> LENGTH: 176
<212> TYPE: DNA
<213> ORGANISM: Artificial Sequence
<220> FEATURE:
<223> OTHER INFORMATION: Description of Artificial Sequence: A fusion
      gene for the expression of a Pep1/Pep2 fusion protein

<400> SEQUENCE: 7
ccggatccgg aattcgtcga ccatgttaaa acatatagta tgggcaagca gggagctaga     60
acgattcaga tctggtggag gcggttcagg cggaggtggc tcgggaggtg gaggatcgct    120
agaacgattc gcagttaatc ctggcctgtt agaaacatca tgataagaat tccggc        176

<210> SEQ ID NO 8
<211> LENGTH: 72
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
ccggatccgg aattcgtcga ccatgttaaa acatatagta tgggcaagca gggagctaga     60
acgattcaga tc                                                         72

<210> SEQ ID NO 9
<211> LENGTH: 104
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
tggtggaggc ggttcaggcg gaggtggctc gggaggtgga ggatcgctag aacgattcgc     60
agttaatcct ggcctgttag aaacatcatg ataagaattc cggc                     104

<210> SEQ ID NO 10
<211> LENGTH: 68
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
tgaatcgttc tagctccctg cttgcccata ctatatgttt aacatggtcg acgaattcc     60 ggatccgg                                                              68
```

```
<210> SEQ ID NO 11
<211> LENGTH: 108
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
gccggaattc ttaacatgat gtttctaaca ggccaggatt aactgcgaat cgttctagcg      60
atcctccacc tcccgagcca cctccgcctg aaccgcctcc accagatc                  108

<210> SEQ ID NO 12
<211> LENGTH: 222
<212> TYPE: DNA
<213> ORGANISM: Artificial Sequence
<220> FEATURE:
<223> OTHER INFORMATION: Description of Artificial Sequence: Synthetic
      sequence

<400> SEQUENCE: 12
gtcgacgccg gccaagacag cacagacaga ttgacctatt ggggtgtttc gcgagtgtga      60
gagggaagcg ccgcggcctg tatttctaga cctgcccttc gcctggttcg tggcgccttg     120
tgaccccggg cccctgccgc ctgcaagtcg aaattgcgct gtgctcctgt gctacggcct     180
gtggctggac tgcctgctgc tgcccaactg gagcgtccat gg                        222

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 13
ggcagatctt cgacgccggc c                                                21

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 14
ggccggaatt ccctcgagag aggatccttg ggcagcagc                             39

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 15
ggccgaattc gtcgacacca tgggtgcgag cg                                    32

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 16
ccggaattca ctcgagatct gtaattttgg ctgacc                                36
```

```
<210> SEQ ID NO 17
<211> LENGTH: 396
<212> TYPE: DNA
<213> ORGANISM: Human immunodeficiency virus

<400> SEQUENCE: 17
atgggtgcga gagcgtcagt attaagcggg ggagaattag atcgatggga aaaaattcgg      60
ttaaggccag ggggaaagaa aaatataaa ttaaaacata tagtatgggc aagcagggag       120
ctagaacgat tcgcagttaa tcctggcctg ttagaaacat cagaaggctg tagacaaata     180
ctgggacagc tacaaccatc ccttcagaca ggatcagaag aacttagatc attatataat     240
acagtagcaa ccctctattg tgtgcatcaa aggatagaga taaaagacac caaggaagct     300
ttagacaaga tagaggaaga gcaaaacaaa agtaagaaaa aagcacagca agcagcagct     360
gacacaggac acagcagcca ggtcagccaa aattac                              396

<210> SEQ ID NO 18
<211> LENGTH: 132
<212> TYPE: PRT
<213> ORGANISM: Human immunodeficiency virus

<400> SEQUENCE: 18

Met Gly Ala Arg Ala Ser Val Leu Ser Gly Gly Glu Leu Asp Arg Trp
 1               5                  10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Ser Gln Val
        115                 120                 125

Ser Gln Asn Tyr
    130

<210> SEQ ID NO 19
<211> LENGTH: 15
<212> TYPE: PRT
<213> ORGANISM: Artificial Sequence
<220> FEATURE:
<221> NAME/KEY: SITE
<222> LOCATION: (4)
<223> OTHER INFORMATION: Xaa=Ile or Val
<223> OTHER INFORMATION: Description of Artificial Sequence: Consensus
      sequence

<400> SEQUENCE: 19

Leu Lys His Xaa Val Trp Ala Ala Asn Glu Leu Asp Arg Phe Gly
 1               5                  10                  15

<210> SEQ ID NO 20
<211> LENGTH: 16
<212> TYPE: PRT
<213> ORGANISM: Artificial Sequence
<220> FEATURE:
```

```
<223> OTHER INFORMATION: Description of Artificial Sequence: Consensus
      sequence

<400> SEQUENCE: 20

Leu Asp Arg Phe Gly Leu Ala Glu Ser Leu Leu Glu Ser Lys Glu Gly
 1               5                  10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Linker

<400> SEQUENCE: 21

Gly Gly Gly Gly Ser Gly Gly Gly Gly Ser Gly Gly Gly Gly Ser
 1               5                  10                  15

<210> SEQ ID NO 22
<211> LENGTH: 21
<212> TYPE: PRT
<213> ORGANISM: Artificial Sequence
<220> FEATURE:
<223> OTHER INFORMATION: Description of Artificial Sequence: Linker

<400> SEQUENCE: 22

Asn Phe Ile Arg Gly Arg Glu Asp Leu Leu Glu Lys Ile Ile Arg Gln
 1               5                  10                  15

Lys Gly Ser Ser Asn
             20

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence: Linker

<400> SEQUENCE: 23

Asn Leu Ser Ser Asp Ser Ser Leu Ser Ser Pro Ser Ala Leu Asn Ser
 1               5                  10                  15

Pro Gly Ile Glu Gly Leu Ser
             20

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Linker

<400> SEQUENCE: 24

Gln Gly Ala Thr Phe Ala Leu Arg Gly Asp Asn Pro Gln Gly
 1               5                  10

<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence: Linker
```

```
<400> SEQUENCE: 25

Ser Gly Gly Gly Glu Ile Leu Asp Val Pro Ser Thr Gly Gly Ser Ser
 1               5                  10                  15

Pro Gly

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Linker

<400> SEQUENCE: 26

Gly Gly Gly Gly Ser
 1               5

<210> SEQ ID NO 27
<211> LENGTH: 70
<212> TYPE: PRT
<213> ORGANISM: Artificial Sequence
<220> FEATURE:
<221> NAME/KEY: SITE
<222> LOCATION: (54)
<223> OTHER INFORMATION: Xaa=Ala, Thr, Gly, Lys, Ser, or Val
<223> OTHER INFORMATION: Description of Artificial Sequence: Consensus
      sequence

<400> SEQUENCE: 27

Met Gly Ala Arg Ala Ser Val Leu Ser Gly Gly Lys Leu Asp Ala Trp
 1               5                  10                  15

Glu Lys Ile Arg Leu Arg Pro Gly Gly Lys Lys Lys Tyr Arg Leu Lys
                20                  25                  30

His Leu Val Trp Ala Ser Arg Glu Leu Glu Arg Phe Ala Leu Asn Pro
            35                  40                  45

Ser Leu Leu Glu Thr Xaa Glu Gly Cys Gln Gln Ile Met Glu Gln Leu
        50                  55                  60

Gln Ser Ala Leu Lys Thr
 65                  70

<210> SEQ ID NO 28
<211> LENGTH: 70
<212> TYPE: PRT
<213> ORGANISM: Artificial Sequence
<220> FEATURE:
<223> OTHER INFORMATION: Description of Artificial Sequence: Consensus
      sequence

<400> SEQUENCE: 28

Met Gly Ala Arg Ala Ser Val Leu Ser Gly Glu Leu Asp Arg Trp
 1               5                  10                  15

Glu Lys Ile Arg Leu Arg Pro Gly Gly Lys Lys Lys Tyr Lys Leu Lys
                20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
        50                  55                  60

Gln Pro Ser Leu Gln Thr
 65                  70

<210> SEQ ID NO 29
<211> LENGTH: 70
<212> TYPE: PRT
```

```
<213> ORGANISM: Artificial Sequence
<220> FEATURE:
<221> NAME/KEY: SITE
<222> LOCATION: (15)
<223> OTHER INFORMATION: Xaa=Thr, Ala, or Lys
<223> OTHER INFORMATION: Description of Artificial Sequence: Consensus
      sequence

<400> SEQUENCE: 29

Met Gly Ala Arg Ala Ser Ile Leu Arg Gly Gly Lys Leu Asp Xaa Trp
  1               5                  10                  15

Glu Lys Ile Arg Leu Arg Pro Gly Gly Lys Lys His Tyr Met Ile Lys
             20                  25                  30

His Leu Val Trp Ala Ser Arg Glu Leu Glu Arg Phe Ala Leu Asn Pro
         35                  40                  45

Gly Leu Leu Glu Thr Ser Glu Gly Cys Lys Gln Ile Ile Lys Gln Leu
     50                  55                  60

Gln Pro Ala Leu Gln Thr
 65                  70

<210> SEQ ID NO 30
<211> LENGTH: 70
<212> TYPE: PRT
<213> ORGANISM: Artificial Sequence
<220> FEATURE:
<221> NAME/KEY: SITE
<222> LOCATION: (15)
<223> OTHER INFORMATION: Xaa=Lys, Thr, Ala, Ser, Gln, Glu, or Arg
<223> OTHER INFORMATION: Description of Artificial Sequence: Consensus
      sequence
<221> NAME/KEY: SITE
<222> LOCATION: (30)
<223> OTHER INFORMATION: Xaa=Arg, Ala, Gln, or Lys

<400> SEQUENCE: 30

Met Gly Ala Arg Ala Ser Val Leu Ser Gly Gly Lys Leu Asp Xaa Trp
  1               5                  10                  15

Glu Lys Ile Arg Leu Arg Pro Gly Gly Lys Lys Lys Tyr Xaa Leu Lys
             20                  25                  30

His Ile Val Trp Ala Ser Arg Glu Leu Glu Arg Phe Ala Leu Asn Pro
         35                  40                  45

Gly Leu Leu Glu Thr Ser Glu Gly Cys Lys Gln Ile Ile Gly Gln Leu
     50                  55                  60

Gln Pro Ala Ile Gln Thr
 65                  70

<210> SEQ ID NO 31
<211> LENGTH: 70
<212> TYPE: PRT
<213> ORGANISM: Artificial Sequence
<220> FEATURE:
<223> OTHER INFORMATION: Description of Artificial Sequence: Consensus
      sequence

<400> SEQUENCE: 31

Met Gly Ala Arg Ala Ser Val Leu Ser Gly Gly Lys Leu Asp Ala Trp
  1               5                  10                  15

Glu Lys Ile Arg Leu Arg Pro Gly Gly Lys Lys Lys Tyr Arg Met Lys
             20                  25                  30

His Leu Val Trp Ala Ser Arg Glu Leu Glu Arg Phe Ala Ile Asp Pro
         35                  40                  45
```

```
Gly Leu Leu Glu Thr Ser Glu Gly Cys Arg Lys Ile Ile Gly Gln Leu
        50                  55                  60

Gln Pro Ser Leu Gln Thr
 65                  70

<210> SEQ ID NO 32
<211> LENGTH: 70
<212> TYPE: PRT
<213> ORGANISM: Artificial Sequence
<220> FEATURE:
<221> NAME/KEY: SITE
<222> LOCATION: (54)
<223> OTHER INFORMATION: Xaa=Thr, Ser, Ala, or Lys
<221> NAME/KEY: SITE
<222> LOCATION: (58)
<223> OTHER INFORMATION: Xaa=Gln, Leu, Arg, Glu, or Thr
<221> NAME/KEY: SITE
<222> LOCATION: (60)
<223> OTHER INFORMATION: Xaa=Ile or Leu
<221> NAME/KEY: SITE
<222> LOCATION: (61)
<223> OTHER INFORMATION: Xaa=Met, Leu, or Ile
<221> NAME/KEY: SITE
<222> LOCATION: (62)
<223> OTHER INFORMATION: Xaa=Arg, Gln, or Glu
<223> OTHER INFORMATION: Description of Artificial Sequence: Consensus
      sequence

<400> SEQUENCE: 32

Met Gly Ala Arg Ala Ser Val Leu Ser Gly Gly Lys Leu Asp Ala Trp
 1               5                  10                  15

Glu Lys Ile Arg Leu Arg Pro Gly Gly Lys Lys Lys Tyr Arg Leu Lys
                20                  25                  30

His Leu Val Trp Ala Ser Arg Glu Leu Glu Arg Phe Ala Leu Asn Pro
            35                  40                  45

Gly Leu Leu Glu Thr Xaa Glu Gly Cys Xaa Gln Xaa Xaa Xaa Gln Leu
        50                  55                  60

Gln Pro Ala Leu Lys Thr
 65                  70

<210> SEQ ID NO 33
<211> LENGTH: 140
<212> TYPE: PRT
<213> ORGANISM: Artificial Sequence
<220> FEATURE:
<221> NAME/KEY: SITE
<222> LOCATION: (34)
<223> OTHER INFORMATION: Xaa=Ile or Val
<221> NAME/KEY: SITE
<222> LOCATION: (79)
<223> OTHER INFORMATION: Xaa=Phe or Tyr
<221> NAME/KEY: SITE
<222> LOCATION: (96)
<223> OTHER INFORMATION: Xaa=Asp or His
<221> NAME/KEY: SITE
<222> LOCATION: (120)
<223> OTHER INFORMATION: Xaa=Ser, Asn, Asp, Ala, or Lys
<221> NAME/KEY: SITE
<222> LOCATION: (140)
<223> OTHER INFORMATION: Xaa=Thr, or absent
<223> OTHER INFORMATION: Description of Artificial Sequence: Consensus
      sequence

<400> SEQUENCE: 33

Met Gly Ala Arg Asn Ser Val Leu Ser Gly Lys Lys Ala Asp Glu Leu
 1               5                  10                  15

Glu Lys Ile Arg Leu Arg Pro Gly Gly Lys Lys Lys Tyr Met Leu Lys
                20                  25                  30
```

```
His Xaa Val Trp Ala Ala Asn Glu Leu Asp Arg Phe Gly Leu Ala Glu
        35                  40                  45

Ser Leu Leu Glu Ser Lys Glu Gly Cys Gln Lys Ile Leu Ser Val Leu
 50                  55                  60

Ala Pro Leu Val Pro Thr Gly Ser Glu Asn Leu Lys Ser Leu Xaa Asn
 65                  70                  75                  80

Thr Val Cys Val Ile Trp Cys Ile His Ala Glu Glu Lys Val Lys Xaa
                 85                  90                  95

Thr Glu Glu Ala Lys Gln Ile Val Gln Arg His Leu Val Ala Glu Thr
                100                 105                 110

Gly Thr Ala Glu Lys Met Pro Xaa Thr Ser Arg Pro Thr Ala Pro Pro
            115                 120                 125

Ser Gly Arg Gly Gly Asn Tyr Pro Val Gln Gln Xaa
            130                 135                 140

<210> SEQ ID NO 34
<211> LENGTH: 70
<212> TYPE: PRT
<213> ORGANISM: Human immunodeficiency virus type 1

<400> SEQUENCE: 34

Met Gly Ala Arg Ala Ser Val Leu Ser Gly Lys Lys Leu Asp Ser Trp
 1               5                  10                  15

Glu Lys Ile Arg Leu Arg Pro Gly Gly Asn Lys Lys Tyr Arg Leu Lys
                20                  25                  30

His Leu Val Trp Ala Ser Arg Glu Leu Glu Lys Phe Thr Leu Asn Pro
            35                  40                  45

Gly Leu Leu Glu Thr Ala Glu Gly Cys Gln Gln Ile Met Gly Gln Leu
 50                  55                  60

Gln Pro Ala Leu Gln Thr
 65                  70

<210> SEQ ID NO 35
<211> LENGTH: 68
<212> TYPE: PRT
<213> ORGANISM: Human immunodeficiency virus type 1

<400> SEQUENCE: 35

Met Gly Ala Arg Val Ser Val Leu Ser Glu Gly Lys Leu Asp Ala Glu
 1               5                  10                  15

Lys Ile Arg Leu Arg Pro Glu Gly Lys Lys Tyr Lys Leu Lys His
            20                  25                  30

Leu Val Ala Ser Arg Glu Leu Glu Lys Phe Ala Leu Asn Pro Ser Leu
            35                  40                  45

Leu Glu Thr Thr Glu Gly Cys Gln Arg Ile Leu Glu Gln Leu Gln Pro
 50                  55                  60

Ala Leu Gln Thr
 65

<210> SEQ ID NO 36
<211> LENGTH: 70
<212> TYPE: PRT
<213> ORGANISM: Human immunodeficiency virus type 1

<400> SEQUENCE: 36

Met Gly Ala Arg Ala Ser Val Leu Ser Gly Gly Lys Leu Asp Ala Trp
 1               5                  10                  15
```

-continued

Glu Lys Ile Arg Leu Arg Pro Gly Gly Lys Lys Tyr Arg Leu Lys
            20                  25                  30

His Leu Val Trp Ala Ser Arg Glu Leu Glu Arg Phe Ala Leu Asn Pro
        35                  40                  45

Gly Leu Leu Glu Thr Gly Glu Gly Cys Gln Gln Ile Met Glu Gln Leu
    50                  55                  60

Gln Ser Thr Leu Lys Thr
65                  70

<210> SEQ ID NO 37
<211> LENGTH: 70
<212> TYPE: PRT
<213> ORGANISM: Human immunodeficiency virus type 1

<400> SEQUENCE: 37

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Tyr Arg Met Lys
            20                  25                  30

His Leu Val Trp Ala Ser Arg Glu Leu Asp Arg Phe Ala Leu Asn Pro
        35                  40                  45

Ser Leu Leu Glu Thr Lys Glu Gly Cys Gln Gln Ile Met Glu Gln Leu
    50                  55                  60

Glu Ser Ala Leu Lys Thr
65                  70

<210> SEQ ID NO 38
<211> LENGTH: 70
<212> TYPE: PRT
<213> ORGANISM: Human immunodeficiency virus type 1

<400> SEQUENCE: 38

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Lys Tyr Arg Leu Lys
            20                  25                  30

His Leu Val Trp Ala Ser Arg Glu Leu Glu Arg Phe Ala Leu Asn Pro
        35                  40                  45

Ser Leu Leu Glu Thr Thr Glu Gly Cys Gln Gln Ile Leu Glu Gln Leu
    50                  55                  60

Gln Pro Ala Leu Lys Thr
65                  70

<210> SEQ ID NO 39
<211> LENGTH: 70
<212> TYPE: PRT
<213> ORGANISM: Human immunodeficiency virus type 1
<220> FEATURE:
<221> NAME/KEY: SITE
<222> LOCATION: (16,36)
<223> OTHER INFORMATION: Xaa=undetermined

<400> SEQUENCE: 39

Ile Gly Ala Arg Ala Ser Val Leu Ser Glu Gly Lys Leu Asp Ala Xaa
1               5                   10                  15

Glu Lys Ile Arg Leu Arg Pro Gly Gly Lys Lys Gln Tyr Arg Leu Lys
            20                  25                  30

His Leu Val Xaa Ala Ser Lys Glu Leu Glu Arg Phe Ala Leu Asn Pro
        35                  40                  45

-continued

Ser Leu Leu Glu Thr Thr Glu Gly Cys Gln Gln Ile Ile Glu Gln Leu
            50                  55                  60

Gln Pro Ala Leu Lys Thr
 65                  70

<210> SEQ ID NO 40
<211> LENGTH: 70
<212> TYPE: PRT
<213> ORGANISM: Human immunodeficiency virus type 1

<400> SEQUENCE: 40

Met Gly Ala Arg Ala Ser Val Leu Ser Gly Gly Lys Leu Asp Lys Trp
  1               5                  10                  15

Glu Lys Ile Arg Leu Arg Pro Gly Gly Lys Lys Gln Tyr Arg Leu Lys
                 20                  25                  30

His Leu Val Trp Ala Ser Arg Glu Leu Glu Arg Phe Ala Leu Asn Pro
             35                  40                  45

Ser Leu Leu Glu Thr Thr Glu Gly Cys Gln Gln Ile Ile Glu Gln Leu
            50                  55                  60

Gln Pro Ala Leu Lys Thr
 65                  70

<210> SEQ ID NO 41
<211> LENGTH: 70
<212> TYPE: PRT
<213> ORGANISM: Human immunodeficiency virus type 1

<400> SEQUENCE: 41

Met Gly Ala Arg Ala Ser Ile Leu Ser Gly Gly Lys Leu Asp Ala Trp
  1               5                  10                  15

Lys Arg Ile Arg Leu Arg Pro Gly Gly Lys Lys Lys Tyr Gln Ile Lys
                 20                  25                  30

His Ile Val Trp Ala Ser Arg Lys Leu Glu Lys Phe Ala Leu Asn Pro
             35                  40                  45

Gly Leu Leu Lys Thr Ala Glu Gly Cys Gln Gln Ile Met Glu Gln Leu
            50                  55                  60

Gln Ser Ala Leu Lys Thr
 65                  70

<210> SEQ ID NO 42
<211> LENGTH: 70
<212> TYPE: PRT
<213> ORGANISM: Human immunodeficiency virus type 1

<400> SEQUENCE: 42

Met Gly Ala Arg Ala Ser Val Leu Ser Gly Gly Lys Leu Asp Ala Trp
  1               5                  10                  15

Glu Lys Ile Arg Leu Arg Pro Gly Gly Arg Lys Lys Tyr Arg Met Lys
                 20                  25                  30

His Leu Val Trp Ala Ser Arg Glu Leu Asp Arg Phe Ala Leu Asn Pro
             35                  40                  45

Gly Leu Leu Glu Thr Ala Glu Gly Cys Gln Gln Ile Leu Glu Gln Leu
            50                  55                  60

Gln Pro Ala Leu Lys Thr
 65                  70

<210> SEQ ID NO 43
<211> LENGTH: 70
<212> TYPE: PRT

<213> ORGANISM: Human immunodeficiency virus type 1
<220> FEATURE:
<221> NAME/KEY: SITE
<222> LOCATION: (16)
<223> OTHER INFORMATION: Xaa=undetermined

<400> SEQUENCE: 43

Ile Gly Ala Arg Ala Ser Val Leu Ser Gly Gly Gln Leu Asp Arg Xaa
1               5                   10                  15

Glu Lys Ile Arg Leu Arg Pro Gly Gly Lys Lys Lys Tyr Arg Leu Lys
                20                  25                  30

His Leu Val Trp Ala Ser Arg Glu Leu Glu Arg Phe Ala Leu Asn Pro
            35                  40                  45

Ser Leu Leu Glu Thr Thr Glu Arg Cys Gln Gln Ile Met Glu Gln Leu
        50                  55                  60

Gln Ser Ala Leu Lys Thr
65                  70

<210> SEQ ID NO 44
<211> LENGTH: 70
<212> TYPE: PRT
<213> ORGANISM: Human immunodeficiency virus type 1

<400> SEQUENCE: 44

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Lys Tyr Arg Met Lys
                20                  25                  30

His Leu Val Trp Ala Ser Arg Glu Leu Glu Arg Phe Ala Leu Asn Pro
            35                  40                  45

Ser Leu Leu Glu Thr Thr Glu Gly Cys Gln Gln Ile Ile Glu Gln Leu
        50                  55                  60

Gln Pro Ala Leu Lys Thr
65                  70

<210> SEQ ID NO 45
<211> LENGTH: 70
<212> TYPE: PRT
<213> ORGANISM: Human immunodeficiency virus type 1

<400> SEQUENCE: 45

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Lys Tyr Met Leu Lys
                20                  25                  30

His Leu Val Trp Ala Ser Arg Glu Leu Asp Arg Phe Ala Leu Asn Pro
            35                  40                  45

Ser Leu Leu Glu Thr Ala Glu Gly Cys Gln Gln Ile Met Glu Gln Leu
        50                  55                  60

Gln Ser Ala Leu Lys Thr
65                  70

<210> SEQ ID NO 46
<211> LENGTH: 70
<212> TYPE: PRT
<213> ORGANISM: Human immunodeficiency virus type 1

<400> SEQUENCE: 46

Met Gly Ala Arg Ala Ser Val Leu Ser Gly Gly Lys Leu Asp Thr Trp
1               5                   10                  15

-continued

Glu Lys Ile Arg Leu Arg Pro Gly Gly Lys Lys Tyr Lys Leu Lys
                20                  25                  30

His Leu Val Trp Ala Ser Arg Glu Leu Glu Arg Phe Ala Leu Asn Pro
            35                  40                  45

Ser Leu Leu Glu Thr Thr Glu Gly Cys Gln Gln Ile Met Glu Gln Leu
        50                  55                  60

Gln Pro Ala Leu Lys Thr
 65              70

<210> SEQ ID NO 47
<211> LENGTH: 70
<212> TYPE: PRT
<213> ORGANISM: Human immunodeficiency virus type 1

<400> SEQUENCE: 47

Met Gly Ala Arg Thr Ser Val Leu Ser Gly Gly Lys Leu Asp Ala Trp
 1               5                  10                  15

Glu Lys Ile Arg Leu Arg Pro Gly Gly Asn Lys Arg Tyr Lys Leu Lys
                20                  25                  30

His Ile Val Trp Ala Ser Arg Glu Leu Glu Arg Phe Ala Leu Asn Pro
            35                  40                  45

Gly Leu Leu Glu Thr Thr Glu Gly Cys Gln Gln Ile Met Lys Gln Leu
        50                  55                  60

Gln Ser Ala Leu Gln Thr
 65              70

<210> SEQ ID NO 48
<211> LENGTH: 70
<212> TYPE: PRT
<213> ORGANISM: Human immunodeficiency virus type 1

<400> SEQUENCE: 48

Met Gly Ala Arg Ala Ser Val Leu Ser Gly Gly Lys Leu Asp Ala Trp
 1               5                  10                  15

Glu Lys Ile Arg Leu Arg Pro Gly Gly Lys Lys Lys Tyr Arg Leu Lys
                20                  25                  30

His Leu Val Trp Ala Ser Arg Glu Leu Glu Lys Phe Ala Leu Asn Pro
            35                  40                  45

Ser Leu Leu Glu Thr Thr Glu Gly Cys Gln Gln Ile Met Glu Gln Leu
        50                  55                  60

Gln Ser Ala Leu Lys Thr
 65              70

<210> SEQ ID NO 49
<211> LENGTH: 70
<212> TYPE: PRT
<213> ORGANISM: Human immunodeficiency virus type 1

<400> SEQUENCE: 49

Met Gly Ala Arg Ala Ser Val Leu Ser Gly Gly Lys Leu Asp Ala Trp
 1               5                  10                  15

Glu Lys Ile Arg Leu Arg Pro Gly Gly Lys Lys Lys Tyr Arg Leu Lys
                20                  25                  30

His Leu Val Trp Ala Ser Arg Glu Leu Glu Arg Phe Ala Leu Asn Pro
            35                  40                  45

```
Ser Leu Leu Glu Thr Thr Glu Gly Cys Gln Gln Ile Met Glu Gln Leu
 50                  55                  60

Gln Ser Ser Leu Lys Thr
 65                  70
```

<210> SEQ ID NO 50
<211> LENGTH: 70
<212> TYPE: PRT
<213> ORGANISM: Human immunodeficiency virus type 1

<400> SEQUENCE: 50

```
Met Gly Ala Arg Ala Ser Val Leu Ser Gly Gly Lys Leu Asp Ala Trp
 1               5                  10                  15

Glu Lys Ile Arg Leu Arg Pro Gly Gly Lys Lys Lys Tyr Arg Met Lys
                20                  25                  30

His Leu Ile Trp Ala Gly Arg Glu Leu Glu Arg Phe Ala Leu Asn Pro
             35                  40                  45

Ser Leu Leu Glu Thr Thr Glu Gly Cys Gln Gln Ile Met Glu Gln Leu
 50                  55                  60

Gln Ser Ala Leu Lys Thr
 65                  70
```

<210> SEQ ID NO 51
<211> LENGTH: 70
<212> TYPE: PRT
<213> ORGANISM: Human immunodeficiency virus type 1

<400> SEQUENCE: 51

```
Met Gly Ala Arg Ala Ser Val Leu Ser Gly Gly Lys Leu Asp Ala Trp
 1               5                  10                  15

Glu Lys Ile Arg Leu Arg Pro Gly Gly Lys Lys Lys Tyr Arg Leu Lys
                20                  25                  30

His Leu Val Trp Ala Ser Arg Glu Leu Glu Arg Phe Ala Leu Asn Pro
             35                  40                  45

Ser Leu Leu Glu Thr Ala Gly Gly Cys Gln Gln Leu Met Glu Gln Leu
 50                  55                  60

Gln Ala Ala Leu Arg Thr
 65                  70
```

<210> SEQ ID NO 52
<211> LENGTH: 70
<212> TYPE: PRT
<213> ORGANISM: Human immunodeficiency virus type 1

<400> SEQUENCE: 52

```
Met Gly Ala Arg Ala Ser Val Leu Ser Gly Gly Arg Leu Asp Ala Trp
 1               5                  10                  15

Glu Lys Ile Arg Leu Arg Pro Gly Gly Lys Lys Lys Tyr Lys Leu Lys
                20                  25                  30

His Leu Val Trp Ala Ser Arg Glu Leu Glu Arg Phe Ala Leu Asn Pro
             35                  40                  45

Ser Leu Leu Glu Thr Ser Glu Gly Cys Gln Gln Leu Ile Glu Gln Phe
 50                  55                  60

Gln Ser Thr Leu Gly Thr
 65                  70
```

<210> SEQ ID NO 53
<211> LENGTH: 70

```
<212> TYPE: PRT
<213> ORGANISM: Human immunodeficiency virus type 1

<400> SEQUENCE: 53

Met Gly Ala Arg Ala Ser Ile Leu Ser Gly Gly Lys Leu Asp Ser Trp
 1               5                  10                  15

Glu Lys Ile Arg Leu Arg Pro Gly Gly Arg Lys Lys Gln Arg Leu Lys
            20                  25                  30

His Leu Val Trp Ala Ser Arg Glu Leu Glu Arg Phe Ala Leu Asn Pro
        35                  40                  45

Ser Leu Leu Glu Thr Ala Glu Gly Cys Gln Gln Ile Ile Glu Gln Leu
    50                  55                  60

Gln Ser Ala Leu Lys Thr
65                  70

<210> SEQ ID NO 54
<211> LENGTH: 70
<212> TYPE: PRT
<213> ORGANISM: Human immunodeficiency virus type 1

<400> SEQUENCE: 54

Met Gly Ala Arg Ala Ser Val Leu Ser Gly Gly Lys Leu Asp Ala Trp
 1               5                  10                  15

Glu Lys Ile Arg Leu Arg Pro Gly Gly Lys Lys Lys Tyr Arg Leu Lys
            20                  25                  30

His Leu Val Trp Ala Ser Arg Glu Leu Glu Arg Phe Ala Leu Asn Pro
        35                  40                  45

Gly Leu Leu Glu Thr Ala Asp Gly Cys Gln Gln Leu Met Glu Gln Leu
    50                  55                  60

Gln Ser Ala Leu Arg Thr
65                  70

<210> SEQ ID NO 55
<211> LENGTH: 70
<212> TYPE: PRT
<213> ORGANISM: Human immunodeficiency virus type 1

<400> SEQUENCE: 55

Met Gly Ala Arg Ala Ser Val Leu Ser Gly Gly Lys Leu Asp Asp Trp
 1               5                  10                  15

Glu Lys Ile Gln Leu Arg Pro Gly Gly Thr Lys Arg Tyr Lys Leu Lys
            20                  25                  30

His Ile Val Trp Ala Ser Arg Glu Leu Glu Arg Phe Ala Leu Asp Pro
        35                  40                  45

Ser Leu Leu Glu Thr Ser Glu Gly Cys Lys Gln Ile Leu Gly Gln Leu
    50                  55                  60

Gln Pro Ala Leu Lys Thr
65                  70

<210> SEQ ID NO 56
<211> LENGTH: 70
<212> TYPE: PRT
<213> ORGANISM: Human immunodeficiency virus type 1

<400> SEQUENCE: 56

Met Gly Ala Arg Ala Ser Val Leu Thr Gly Gly Lys Leu Asp Ala Trp
 1               5                  10                  15

Glu Lys Ile Arg Leu Arg Pro Gly Gly Arg Lys Lys Tyr Lys Leu Lys
            20                  25                  30
```

His Leu Val Trp Ala Ser Arg Glu Leu Glu Arg Phe Ala Leu Asn Pro
            35                  40                  45

Gly Leu Leu Glu Thr Val Glu Gly Cys Gln Gln Ile Ile Glu Gln Leu
        50                  55                  60

Gln Ser Thr Leu Lys Thr
65                  70

<210> SEQ ID NO 57
<211> LENGTH: 70
<212> TYPE: PRT
<213> ORGANISM: Human immunodeficiency virus type 1

<400> SEQUENCE: 57

Met Gly Ala Arg Ala Ser Val Leu Ser Gly Gly Lys Leu Asp Ala Trp
1               5                   10                  15

Glu Lys Ile Arg Leu Arg Pro Gly Gly Arg Lys Lys Tyr Arg Met Lys
            20                  25                  30

His Leu Val Trp Ala Ser Arg Glu Leu Glu Arg Phe Ala Leu Asn Pro
            35                  40                  45

Gly Leu Leu Glu Thr Ala Glu Gly Cys Gln Gln Ile Ile Glu Gln Leu
        50                  55                  60

Gln Ser Thr Leu Lys Thr
65                  70

<210> SEQ ID NO 58
<211> LENGTH: 70
<212> TYPE: PRT
<213> ORGANISM: Human immunodeficiency virus type 1

<400> SEQUENCE: 58

Met Gly Ala Arg Ala Ser Val Leu Ser Gly Gly Lys Leu Asp Ala Trp
1               5                   10                  15

Glu Lys Ile Arg Leu Arg Pro Gly Gly Arg Lys Lys Tyr Arg Leu Lys
            20                  25                  30

His Leu Val Trp Ala Ser Arg Glu Leu Glu Arg Phe Ala Leu Asn Pro
            35                  40                  45

Ser Phe Leu Glu Thr Ala Glu Gly Cys Gln Gln Ile Ile Glu Gln Leu
        50                  55                  60

Gln Ser Thr Leu Lys Thr
65                  70

<210> SEQ ID NO 59
<211> LENGTH: 70
<212> TYPE: PRT
<213> ORGANISM: Human immunodeficiency virus type 1

<400> SEQUENCE: 59

Met Gly Ala Arg Ala Ser Val Leu Ser Gly Gly Lys Leu Asp Ala Trp
1               5                   10                  15

Glu Lys Ile Arg Leu Arg Pro Gly Gly Arg Lys Lys Tyr Lys Met Lys
            20                  25                  30

His Leu Val Trp Ala Ser Arg Glu Leu Glu Arg Phe Ala Leu Asn Pro
            35                  40                  45

Gly Leu Leu Glu Thr Ala Glu Gly Arg Gln Gln Ile Ile Arg Gln Leu
        50                  55                  60

Gln Ser Thr Leu Lys Thr
65                  70

```
<210> SEQ ID NO 60
<211> LENGTH: 70
<212> TYPE: PRT
<213> ORGANISM: Human immunodeficiency virus type 1

<400> SEQUENCE: 60

Met Gly Ala Arg Ala Ser Val Leu Ser Gly Gly Lys Leu Asp Thr Trp
  1               5                  10                  15

Glu Lys Ile Arg Leu Arg Pro Gly Gly Lys Lys Tyr Arg Met Lys
             20                  25                  30

His Leu Val Trp Ala Ser Arg Glu Leu Glu Arg Phe Ala Leu Asn Pro
         35                  40                  45

Gly Leu Leu Glu Thr Ala Glu Gly Cys Gln Gln Ile Leu Glu Gln Leu
     50                  55                  60

Gln Pro Ser Val Lys Thr
 65                  70

<210> SEQ ID NO 61
<211> LENGTH: 70
<212> TYPE: PRT
<213> ORGANISM: Human immunodeficiency virus type 1

<400> SEQUENCE: 61

Met Gly Ala Arg Ala Ser Val Leu Ser Gly Gly Lys Leu Asp Ala Trp
  1               5                  10                  15

Glu Arg Ile Arg Leu Arg Pro Gly Gly Lys Lys Lys Tyr Arg Met Lys
             20                  25                  30

His Leu Val Trp Ala Ser Arg Glu Leu Glu Arg Phe Ala Leu Asn Pro
         35                  40                  45

Gly Leu Leu Glu Thr Ala Glu Gly Cys Gln Gln Ile Met Gly Gln Leu
     50                  55                  60

Gln Thr Ala Leu Gln Thr
 65                  70

<210> SEQ ID NO 62
<211> LENGTH: 70
<212> TYPE: PRT
<213> ORGANISM: Human immunodeficiency virus type 1

<400> SEQUENCE: 62

Met Gly Ala Arg Ala Ser Val Leu Ser Gly Gly Lys Leu Asp Ser Trp
  1               5                  10                  15

Glu Lys Ile Arg Leu Arg Pro Gly Gly Lys Lys Tyr Arg Leu Lys
             20                  25                  30

His Leu Val Trp Ala Ser Arg Glu Leu Glu Arg Phe Ala Leu Asn Pro
         35                  40                  45

Gly Leu Leu Glu Thr Ala Glu Gly Cys Gln Gln Leu Met Glu Gln Leu
     50                  55                  60

Gln Ser Ala Leu Arg Thr
 65                  70

<210> SEQ ID NO 63
<211> LENGTH: 70
<212> TYPE: PRT
<213> ORGANISM: Human immunodeficiency virus type 1

<400> SEQUENCE: 63

Met Gly Ala Arg Ala Ser Val Leu Ser Gly Gly Lys Leu Asp Ala Trp
  1               5                  10                  15
```

Glu Lys Ile Arg Leu Arg Pro Gly Gly Lys Lys Lys Tyr Arg Leu Lys
            20                  25                  30

His Leu Val Trp Ala Ser Arg Glu Leu Glu Arg Phe Ala Leu Asn Pro
            35                  40                  45

Gly Phe Leu Glu Thr Ala Glu Gly Cys Gln Gln Leu Met Glu Gln Leu
        50                  55                  60

Gln Ser Thr Leu Lys Thr
 65              70

<210> SEQ ID NO 64
<211> LENGTH: 70
<212> TYPE: PRT
<213> ORGANISM: Human immunodeficiency virus type 1

<400> SEQUENCE: 64

Met Gly Ala Arg Ala Ser Val Leu Ser Gly Gly Lys Leu Asp Ser Trp
 1               5                  10                  15

Glu Lys Ile Arg Leu Arg Pro Gly Gly Lys Lys Lys Tyr Arg Leu Lys
            20                  25                  30

His Leu Val Trp Ala Ser Arg Glu Leu Glu Arg Phe Ala Leu Asn Pro
            35                  40                  45

Gly Leu Leu Glu Thr Ala Glu Gly Cys Gln Gln Leu Met Glu Gln Leu
        50                  55                  60

Gln Ser Ala Leu Gly Thr
 65              70

<210> SEQ ID NO 65
<211> LENGTH: 70
<212> TYPE: PRT
<213> ORGANISM: Human immunodeficiency virus type 1

<400> SEQUENCE: 65

Met Gly Ala Arg Ala Ser Val Leu Ser Gly Gly Glu Leu Asp Lys Trp
 1               5                  10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
        50                  55                  60

Gln Pro Ser Leu Gln Thr
 65              70

<210> SEQ ID NO 66
<211> LENGTH: 70
<212> TYPE: PRT
<213> ORGANISM: Human immunodeficiency virus type 1

<400> SEQUENCE: 66

Met Gly Ala Arg Ala Ser Val Leu Ser Gly Gly Glu Leu Asp Arg Trp
 1               5                  10                  15

Glu Lys Ile Arg Leu Arg Pro Gly Gly Lys Lys Lys Tyr Arg Leu Lys
            20                  25                  30

His Val Val Trp Ala Ser Arg Glu Leu Glu Arg Phe Ala Val Asn Pro
            35                  40                  45

-continued

Gly Leu Leu Glu Thr Ala Ala Gly Cys Arg Gln Ile Leu Gly Gln Leu
    50                  55                  60

Gln Pro Ser Leu Gln Thr
 65                  70

<210> SEQ ID NO 67
<211> LENGTH: 70
<212> TYPE: PRT
<213> ORGANISM: Human immunodeficiency virus type 1

<400> SEQUENCE: 67

Met Gly Ala Arg Ala Ser Val Leu Ser Gly Gly Lys Leu Asp Lys Trp
 1               5                  10                  15

Glu Lys Ile Arg Leu Arg Pro Gly Gly Lys Lys Arg Tyr Gln Leu Lys
                20                  25                  30

His Ile Val Trp Ala Ser Arg Glu Leu Glu Arg Phe Ala Val Asn Pro
            35                  40                  45

Gly Leu Leu Glu Thr Ala Glu Gly Cys Arg Gln Ile Leu Gly Gln Leu
    50                  55                  60

Gln Pro Ser Leu Gln Thr
 65                  70

<210> SEQ ID NO 68
<211> LENGTH: 70
<212> TYPE: PRT
<213> ORGANISM: Human immunodeficiency virus type 1

<400> SEQUENCE: 68

Met Gly Ala Arg Ala Ser Val Leu Ser Gly Gly Glu Leu Asp Lys Trp
 1               5                  10                  15

Glu Lys Ile Arg Leu Arg Pro Gly Gly Lys Lys Ala Tyr Lys Leu Lys
                20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Lys Ile Leu Gly Gln Leu
    50                  55                  60

Gln Pro Ser Leu Gln Thr
 65                  70

<210> SEQ ID NO 69
<211> LENGTH: 70
<212> TYPE: PRT
<213> ORGANISM: Human immunodeficiency virus type 1

<400> SEQUENCE: 69

Met Gly Ala Arg Ala Ser Val Leu Ser Gly Gly Glu Leu Asp Arg Trp
 1               5                  10                  15

Glu Arg Ile Arg Leu Arg Pro Gly Gly Lys Lys Lys Tyr Lys Leu Lys
                20                  25                  30

His Ile Val Trp Ala Ser Arg Glu Leu Glu Arg Phe Ala Val Asn Pro
            35                  40                  45

Gly Leu Leu Glu Thr Ser Gly Gly Cys Arg Gln Ile Leu Glu Gln Leu
    50                  55                  60

Gln Pro Ala Leu Gln Thr
 65                  70

<210> SEQ ID NO 70
<211> LENGTH: 70

```
<212> TYPE: PRT
<213> ORGANISM: Human immunodeficiency virus type 1

<400> SEQUENCE: 70

Met Gly Ala Arg Ala Ser Val Leu Ser Gly Gly Lys Leu Asp Arg Trp
 1               5                  10                  15

Glu Lys Ile Arg Leu Arg Pro Gly Gly Lys Lys Lys Tyr Gln Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

His Pro Ala Leu Gln Thr
65                  70

<210> SEQ ID NO 71
<211> LENGTH: 70
<212> TYPE: PRT
<213> ORGANISM: Human immunodeficiency virus type 1

<400> SEQUENCE: 71

Met Gly Ala Arg Ala Ser Val Leu Ser Gly Gly Gln Leu Asp Arg Trp
 1               5                  10                  15

Lys Lys Ile Arg Leu Arg Pro Gly Gly Lys Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr
65                  70

<210> SEQ ID NO 72
<211> LENGTH: 70
<212> TYPE: PRT
<213> ORGANISM: Human immunodeficiency virus type 1

<400> SEQUENCE: 72

Met Gly Ala Arg Ala Ser Val Leu Ser Gly Gly Glu Leu Asp Arg Trp
 1               5                  10                  15

Glu Asn Ile Arg Leu Arg Pro Gly Gly Lys Lys Lys Tyr Lys Leu Lys
            20                  25                  30

His Val Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr
65                  70

<210> SEQ ID NO 73
<211> LENGTH: 70
<212> TYPE: PRT
<213> ORGANISM: Human immunodeficiency virus type 1

<400> SEQUENCE: 73

Met Gly Ala Arg Ala Ser Val Leu Ser Gly Gly Glu Leu Asp Arg Trp
 1               5                  10                  15

Glu Lys Ile Arg Leu Arg Pro Gly Gly Lys Lys Lys Tyr Arg Leu Lys
            20                  25                  30
```

```
His Ile Val Trp Ala Ser Arg Glu Leu Glu Arg Phe Ala Val Asn Pro
        35                  40                  45

Gly Leu Leu Glu Ser Ser Glu Gly Cys Arg Gln Ile Leu Gly Gln Leu
    50                  55                  60

Gln Pro Ser Leu Lys Thr
65                  70

<210> SEQ ID NO 74
<211> LENGTH: 70
<212> TYPE: PRT
<213> ORGANISM: Human immunodeficiency virus type 1

<400> SEQUENCE: 74

Met Gly Ala Arg Ala Ser Val Leu Ser Gly Gly Glu Leu Asp Lys Trp
1               5                   10                  15

Glu Lys Ile Arg Leu Arg Pro Gly Gly Lys Lys Lys Tyr Gln Leu Lys
                20                  25                  30

His Ile Val Trp Ala Ser Arg Glu Leu Glu Arg Phe Ala Ile Asn Pro
        35                  40                  45

Gly Leu Leu Glu Thr Ser Glu Gly Cys Arg Gln Ile Leu Gly Gln Leu
    50                  55                  60

Gln Pro Ser Leu Lys Thr
65                  70

<210> SEQ ID NO 75
<211> LENGTH: 70
<212> TYPE: PRT
<213> ORGANISM: Human immunodeficiency virus type 1

<400> SEQUENCE: 75

Met Gly Ala Arg Ala Ser Val Leu Ser Gly Gly Glu Leu Asp Lys Trp
1               5                   10                  15

Glu Lys Ile Arg Leu Arg Pro Gly Gly Lys Lys Gln Tyr Arg Leu Lys
                20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr
65                  70

<210> SEQ ID NO 76
<211> LENGTH: 70
<212> TYPE: PRT
<213> ORGANISM: Human immunodeficiency virus type 1

<400> SEQUENCE: 76

Met Gly Ala Arg Ala Ser Val Leu Ser Gly Gly Glu Leu Asp Lys Trp
1               5                   10                  15

Glu Lys Ile Arg Leu Arg Pro Gly Gly Lys Lys Gln Tyr Lys Leu Lys
                20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr
65                  70
```

```
<210> SEQ ID NO 77
<211> LENGTH: 70
<212> TYPE: PRT
<213> ORGANISM: Human immunodeficiency virus type 1

<400> SEQUENCE: 77

Met Gly Ala Arg Ala Ser Val Leu Ser Gly Gly Glu Leu Asp Arg Trp
 1               5                  10                  15

Glu Lys Ile Arg Leu Arg Pro Gly Gly Lys Lys Gln Tyr Arg Leu Lys
            20                  25                  30

His Ile Val Trp Ala Ser Arg Lys Leu Glu Arg Phe Ala Val Asn Pro
        35                  40                  45

Gly Leu Leu Glu Thr Ser Lys Gly Cys Arg Gln Ile Leu Gly Gln Leu
    50                  55                  60

Gln Pro Ser Leu Gln Thr
65                  70

<210> SEQ ID NO 78
<211> LENGTH: 70
<212> TYPE: PRT
<213> ORGANISM: Human immunodeficiency virus type 1

<400> SEQUENCE: 78

Met Gly Ala Arg Ala Ser Val Leu Ser Gly Gly Glu Leu Asp Lys Trp
 1               5                  10                  15

Glu Lys Ile Arg Leu Arg Pro Gly Gly Lys Lys Lys Tyr Gln Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Met Gly Gln Leu
    50                  55                  60

Gln Pro Ser Leu Gln Thr
65                  70

<210> SEQ ID NO 79
<211> LENGTH: 70
<212> TYPE: PRT
<213> ORGANISM: Human immunodeficiency virus type 1

<400> SEQUENCE: 79

Met Gly Ala Arg Ala Ser Val Leu Ser Gly Gly Lys Leu Asp Arg Trp
 1               5                  10                  15

Glu Lys Ile Arg Leu Arg Pro Arg Gly Lys Lys Arg Tyr Lys Leu Lys
            20                  25                  30

His Ile Val Trp Ala Ser Arg Glu Leu Glu Arg Phe Ala Val Asn Pro
        35                  40                  45

Ser Leu Leu Glu Thr Ala Glu Gly Cys Arg Gln Ile Leu Gly Gln Leu
    50                  55                  60

Gln Pro Ala Leu Gln Thr
65                  70

<210> SEQ ID NO 80
<211> LENGTH: 70
<212> TYPE: PRT
<213> ORGANISM: Human immunodeficiency virus type 1

<400> SEQUENCE: 80

Met Gly Ala Arg Ala Ser Val Leu Ser Gly Gly Glu Leu Asp Arg Trp
 1               5                  10                  15
```

```
Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
        50                  55                  60

Gln Pro Ser Leu Gln Thr
65                  70

<210> SEQ ID NO 81
<211> LENGTH: 70
<212> TYPE: PRT
<213> ORGANISM: Human immunodeficiency virus type 1

<400> SEQUENCE: 81

Met Gly Ala Arg Ala Ser Val Leu Ser Gly Gly Lys Leu Asp Lys Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
            35                  40                  45

Gly Leu Leu Glu Ser Ser Glu Gly Cys Arg Gln Ile Leu Gly Gln Leu
        50                  55                  60

Leu Pro Ala Leu Lys Thr
65                  70

<210> SEQ ID NO 82
<211> LENGTH: 70
<212> TYPE: PRT
<213> ORGANISM: Human immunodeficiency virus type 1

<400> SEQUENCE: 82

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
        50                  55                  60

Gln Pro Ala Leu Gln Thr
65                  70

<210> SEQ ID NO 83
<211> LENGTH: 70
<212> TYPE: PRT
<213> ORGANISM: Human immunodeficiency virus type 1

<400> SEQUENCE: 83

Met Gly Ala Arg Ala Ser Val Leu Ser Ala Gly Glu Leu Asp Lys Trp
1               5                   10                  15

Glu Lys Ile Arg Leu Arg Pro Gly Gly Lys Lys Gln Tyr Arg Leu Lys
            20                  25                  30

His Ile Val Trp Ala Ser Arg Glu Leu Glu Arg Phe Ala Val Asp Pro
            35                  40                  45
```

-continued

Gly Leu Leu Glu Thr Ser Glu Gly Cys Arg Gln Ile Leu Gly Gln Leu
    50                  55                  60

Gln Pro Ser Leu Gln Thr
65                  70

<210> SEQ ID NO 84
<211> LENGTH: 70
<212> TYPE: PRT
<213> ORGANISM: Human immunodeficiency virus type 1

<400> SEQUENCE: 84

Met Gly Ala Arg Ala Ser Val Leu Arg Gly Gly Lys Leu Asp Thr Trp
1               5                   10                  15

Glu Lys Ile Lys Leu Arg Pro Gly Gly Lys Lys Cys Tyr Met Met Lys
                20                  25                  30

His Leu Val Trp Ala Ser Arg Glu Leu Gly Arg Phe Ala Leu Asn Ser
            35                  40                  45

Gly Leu Leu Glu Thr Ser Glu Gly Cys Lys Gln Ile Met Lys Gln Leu
    50                  55                  60

Gln Pro Ala Leu Gln Thr
65                  70

<210> SEQ ID NO 85
<211> LENGTH: 70
<212> TYPE: PRT
<213> ORGANISM: Human immunodeficiency virus type 1

<400> SEQUENCE: 85

Met Gly Ala Arg Ala Ser Ile Leu Arg Gly Gly Lys Leu Asp Ala Trp
1               5                   10                  15

Glu Arg Ile Arg Leu Arg Pro Gly Gly Lys Lys His Tyr Met Ile Lys
                20                  25                  30

His Leu Val Trp Ala Ser Arg Glu Leu Glu Arg Phe Ala Leu Asn Pro
            35                  40                  45

Gly Leu Leu Glu Thr Ser Glu Gly Cys Lys Gln Ile Met Lys Gln Leu
    50                  55                  60

Gln Pro Ala Leu Gln Thr
65                  70

<210> SEQ ID NO 86
<211> LENGTH: 70
<212> TYPE: PRT
<213> ORGANISM: Human immunodeficiency virus type 1

<400> SEQUENCE: 86

Met Gly Ala Arg Ala Ser Ile Leu Lys Gly Gly Lys Leu Asp Thr Trp
1               5                   10                  15

Glu Lys Ile Arg Leu Arg Pro Gly Gly Lys Lys His Tyr Met Ile Lys
                20                  25                  30

His Leu Val Trp Ala Ser Arg Glu Leu Glu Arg Phe Ala Leu Asn Pro
            35                  40                  45

Gly Leu Leu Glu Thr Ser Glu Gly Cys Lys Gln Ile Ile Lys Gln Leu
    50                  55                  60

Gln Pro Ser Ile Gln Thr
65                  70

<210> SEQ ID NO 87
<211> LENGTH: 70
<212> TYPE: PRT

```
<213> ORGANISM: Human immunodeficiency virus type 1
<220> FEATURE:
<221> NAME/KEY: SITE
<222> LOCATION: (9)
<223> OTHER INFORMATION: Xaa=undetermined

<400> SEQUENCE: 87
```

Met Gly Ala Arg Ala Ser Ile Leu Xaa Gly Gly Lys Leu Asp Ala Trp
 1               5                  10                  15

Glu Lys Ile Arg Leu Arg Pro Gly Gly Lys Lys His Tyr Met Ile Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Ile Lys Gln Leu
    50                  55                  60

Gln Pro Ala Leu Gln Thr
65                  70

```
<210> SEQ ID NO 88
<211> LENGTH: 70
<212> TYPE: PRT
<213> ORGANISM: Human immunodeficiency virus type 1

<400> SEQUENCE: 88
```

Met Gly Ala Arg Ala Ser Ile Leu Arg Gly Gly Lys Leu Asp Lys Trp
 1               5                  10                  15

Glu Lys Ile Arg Leu Arg Pro Gly Gly Lys Lys His Tyr Met Ile Lys
            20                  25                  30

His Leu Val Trp Ala Ser Arg Glu Leu Glu Arg Phe Ala Leu Asn Pro
        35                  40                  45

Gly Leu Leu Glu Thr Ala Asp Gly Cys Lys Gln Ile Ile Arg Gln Leu
    50                  55                  60

His Pro Ala Leu Gln Thr
65                  70

```
<210> SEQ ID NO 89
<211> LENGTH: 70
<212> TYPE: PRT
<213> ORGANISM: Human immunodeficiency virus type 1

<400> SEQUENCE: 89
```

Met Gly Ala Arg Ala Ser Ile Leu Arg Gly Glu Lys Leu Asp Ala Trp
 1               5                  10                  15

Glu Lys Ile Lys Leu Arg Pro Gly Gly Arg Lys Arg Tyr Met Leu Lys
            20                  25                  30

His Leu Val Trp Ala Ser Arg Glu Leu Glu Lys Phe Ala Leu Asn Pro
        35                  40                  45

Ser Leu Leu Glu Thr Ser Glu Gly Cys Lys Gln Ile Ile Lys Gln Leu
    50                  55                  60

Gln Pro Ala Leu Gln Thr
65                  70

```
<210> SEQ ID NO 90
<211> LENGTH: 70
<212> TYPE: PRT
<213> ORGANISM: Human immunodeficiency virus type 1

<400> SEQUENCE: 90
```

Met Gly Ala Arg Ala Ser Ile Leu Arg Gly Gly Lys Leu Asp Thr Trp
 1               5                  10                  15

-continued

Glu Arg Ile Lys Leu Lys Pro Gly Gly Lys Lys His Tyr Met Met Lys
            20                  25                  30

His Leu Val Trp Ala Ser Arg Glu Leu Glu Arg Phe Ala Leu Asp Pro
            35                  40                  45

Gly Leu Leu Glu Thr Ser Gln Gly Cys Arg Glu Ile Ile Lys Lys Leu
        50                  55                  60

Gln Pro Ala Leu Gln Thr
65                  70

<210> SEQ ID NO 91
<211> LENGTH: 70
<212> TYPE: PRT
<213> ORGANISM: Human immunodeficiency virus type 1

<400> SEQUENCE: 91

Met Gly Ala Arg Ala Ser Val Leu Ser Gly Gly Lys Leu Asp Lys Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Tyr Ala Leu Asn Pro
            35                  40                  45

Gly Leu Leu Glu Thr Ser Glu Gly Cys Lys Gln Ile Ile Gly Gln Leu
        50                  55                  60

Gln Pro Ala Ile Gln Thr
65                  70

<210> SEQ ID NO 92
<211> LENGTH: 70
<212> TYPE: PRT
<213> ORGANISM: Human immunodeficiency virus type 1

<400> SEQUENCE: 92

Met Gly Ala Arg Ala Ser Val Leu Ser Gly Gly Lys Leu Asp Thr Trp
1               5                   10                  15

Glu Arg Ile Arg Leu Arg Pro Gly Gly Lys Lys Lys Tyr Ala Leu Lys
            20                  25                  30

His Leu Ile Trp Ala Ser Arg Glu Leu Glu Arg Phe Thr Leu Asn Pro
            35                  40                  45

Gly Leu Leu Glu Thr Ser Asp Gly Cys Lys Gln Ile Ile Gly Gln Leu
        50                  55                  60

Gln Pro Ser Ile Arg Thr
65                  70

<210> SEQ ID NO 93
<211> LENGTH: 70
<212> TYPE: PRT
<213> ORGANISM: Human immunodeficiency virus type 1

<400> SEQUENCE: 93

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Lys Tyr Arg Leu Lys
            20                  25                  30

His Leu Val Trp Ala Ser Arg Glu Leu Glu Arg Phe Ala Leu Asn Pro
            35                  40                  45

```
Gly Leu Leu Glu Thr Ser Asp Gly Cys Lys Gln Ile Ile Gly Gln Leu
        50                  55                  60

Gln Pro Ala Ile Arg Thr
 65                  70

<210> SEQ ID NO 94
<211> LENGTH: 70
<212> TYPE: PRT
<213> ORGANISM: Human immunodeficiency virus type 1

<400> SEQUENCE: 94

Met Gly Ala Arg Ala Ser Val Leu Thr Gly Gly Lys Leu Asp Ser Trp
  1               5                  10                  15

Glu Lys Ile Arg Leu Arg Pro Gly Gly Lys Lys Tyr Arg Leu Lys
                20                  25                  30

His Ile Val Trp Ala Ser Arg Glu Leu Glu Arg Phe Ala Leu Asn Pro
            35                  40                  45

Gly Leu Leu Glu Thr Ser Glu Gly Cys Lys Gln Ile Ile Glu Gln Leu
        50                  55                  60

Gln Pro Ser Ile Gln Thr
 65                  70

<210> SEQ ID NO 95
<211> LENGTH: 70
<212> TYPE: PRT
<213> ORGANISM: Human immunodeficiency virus type 1

<400> SEQUENCE: 95

Met Gly Ala Arg Ala Ser Val Leu Ser Gly Gly Lys Leu Asp Gln Trp
  1               5                  10                  15

Glu Lys Ile Arg Leu Arg Pro Gly Lys Ser Lys Lys Tyr Arg Leu Lys
                20                  25                  30

His Ile Val Trp Ala Ser Arg Glu Leu Lys Arg Phe Ala Leu Asn Pro
            35                  40                  45

Gly Leu Leu Glu Thr Ser Glu Gly Cys Arg Gln Ile Ile Glu Gln Leu
        50                  55                  60

Gln Pro Ala Ile Gln Thr
 65                  70

<210> SEQ ID NO 96
<211> LENGTH: 70
<212> TYPE: PRT
<213> ORGANISM: Human immunodeficiency virus type 1

<400> SEQUENCE: 96

Met Gly Ala Arg Ala Ser Val Leu Ser Gly Gly Gln Leu Asp Ala Trp
  1               5                  10                  15

Glu Arg Ile Arg Leu Arg Pro Gly Gly Lys Lys Lys Tyr Gln Leu Lys
                20                  25                  30

His Ile Val Trp Ala Ser Arg Glu Leu Glu Arg Phe Ala Leu Asn Pro
            35                  40                  45

Gly Leu Leu Glu Thr Ala Glu Gly Cys Lys Gln Ile Ile Glu Gln Leu
        50                  55                  60

His Pro Asn Leu Gln Ser
 65                  70

<210> SEQ ID NO 97
<211> LENGTH: 70
```

```
<212> TYPE: PRT
<213> ORGANISM: Human immunodeficiency virus type 1

<400> SEQUENCE: 97

Met Gly Ala Arg Ala Ser Val Leu Ser Gly Gly Lys Leu Asp Glu Trp
  1               5                  10                  15

Glu Lys Ile Gln Leu Arg Pro Gly Gly His Lys Lys Tyr Lys Leu Lys
             20                  25                  30

His Ile Val Trp Ala Ser Arg Glu Leu Glu Arg Phe Ala Ile Asn Pro
         35                  40                  45

Gly Leu Leu Glu Thr Pro Glu Gly Cys Lys Gln Ile Met Gly Gln Leu
     50                  55                  60

His Pro Ala Ile Gln Thr
 65                  70

<210> SEQ ID NO 98
<211> LENGTH: 70
<212> TYPE: PRT
<213> ORGANISM: Human immunodeficiency virus type 1

<400> SEQUENCE: 98

Met Gly Ala Arg Ala Ser Val Leu Ser Gly Gly Lys Leu Asp Glu Trp
  1               5                  10                  15

Glu Lys Ile Arg Leu Arg Pro Gly Gly Asn Lys Lys Tyr Lys Leu Lys
             20                  25                  30

His Ile Val Trp Ala Ser Arg Glu Leu Glu Arg Phe Ala Ile Asn Pro
         35                  40                  45

Gly Leu Leu Glu Thr Ser Glu Gly Cys Lys Gln Ile Met Gly Gln Leu
     50                  55                  60

Gln Pro Ala Leu Lys Thr
 65                  70

<210> SEQ ID NO 99
<211> LENGTH: 70
<212> TYPE: PRT
<213> ORGANISM: Human immunodeficiency virus type 1

<400> SEQUENCE: 99

Met Gly Ala Arg Ala Ser Val Leu Ser Gly Gly Lys Leu Asp Glu Trp
  1               5                  10                  15

Glu Lys Ile Arg Leu Arg Pro Gly Gly Asn Lys Lys Tyr Lys Leu Lys
             20                  25                  30

His Leu Val Trp Ala Ser Arg Glu Leu Glu Arg Phe Ala Leu Asn Pro
         35                  40                  45

Gly Leu Leu Glu Thr Ser Glu Gly Cys Lys Gln Ile Met Gly Gln Leu
     50                  55                  60

Gln Pro Ser Ile Gln Thr
 65                  70

<210> SEQ ID NO 100
<211> LENGTH: 70
<212> TYPE: PRT
<213> ORGANISM: Human immunodeficiency virus type 1

<400> SEQUENCE: 100

Met Gly Ala Arg Ala Ser Val Leu Ser Gly Gly Gln Leu Asp Arg Trp
  1               5                  10                  15

Glu Lys Ile Arg Leu Arg Pro Gly Gly Lys Lys Lys Tyr Lys Leu Lys
             20                  25                  30
```

```
His Ile Val Trp Ala Ser Arg Glu Leu Glu Arg Phe Ala Leu Asn Pro
        35                  40                  45

Gly Leu Leu Glu Thr Ser Glu Gly Cys Arg Gln Ile Ile Gly Gln Leu
    50                  55                  60

Gln Pro Ala Ile Gln Thr
65                  70

<210> SEQ ID NO 101
<211> LENGTH: 70
<212> TYPE: PRT
<213> ORGANISM: Human immunodeficiency virus type 1

<400> SEQUENCE: 101

Met Gly Ala Arg Ala Ser Val Leu Ser Gly Gly Lys Leu Asp Ala Trp
1               5                   10                  15

Glu Lys Ile Gln Leu Arg Pro Gly Gly Lys Lys Lys Tyr Arg Met Lys
                20                  25                  30

His Leu Val Trp Ala Ser Arg Glu Leu Glu Arg Phe Ala Ile Asp Pro
        35                  40                  45

Gly Leu Leu Glu Thr Pro Glu Gly Cys Arg Lys Ile Ile Gly Gln Leu
    50                  55                  60

Gln Thr Ser Leu Gln Thr
65                  70

<210> SEQ ID NO 102
<211> LENGTH: 70
<212> TYPE: PRT
<213> ORGANISM: Human immunodeficiency virus type 1

<400> SEQUENCE: 102

Met Gly Ala Arg Ala Ser Val Leu Ser Gly Gly Lys Leu Asp Ala Trp
1               5                   10                  15

Glu Lys Ile Arg Leu Arg Pro Gly Gly Arg Lys Lys Tyr Arg Met Lys
                20                  25                  30

His Leu Ile Trp Ala Ser Arg Glu Leu Glu Arg Phe Ala Leu Asp Pro
        35                  40                  45

Gly Leu Leu Glu Thr Ser Glu Gly Cys Arg Lys Ile Ile Gly Gln Leu
    50                  55                  60

Gln Pro Ser Leu Gln Thr
65                  70

<210> SEQ ID NO 103
<211> LENGTH: 70
<212> TYPE: PRT
<213> ORGANISM: Human immunodeficiency virus type 1

<400> SEQUENCE: 103

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Lys Tyr Arg Leu Lys
                20                  25                  30

His Leu Val Trp Ala Ser Arg Glu Leu Glu Arg Phe Ala Ile Asn Pro
        35                  40                  45

Gly Leu Leu Glu Thr Ser Glu Gly Cys Gln Lys Ile Ile Gly Gln Leu
    50                  55                  60

Gln Pro Ser Leu Gln Thr
65                  70
```

```
<210> SEQ ID NO 104
<211> LENGTH: 70
<212> TYPE: PRT
<213> ORGANISM: Human immunodeficiency virus type 1

<400> SEQUENCE: 104

Met Gly Ala Arg Ala Ser Val Leu Ser Gly Gly Lys Leu Asp Ala Trp
 1               5                  10                  15

Glu Lys Ile Arg Leu Arg Pro Gly Gly Lys Lys Gln Tyr Arg Leu Lys
            20                  25                  30

His Leu Val Trp Ala Ser Arg Glu Leu Glu Lys Phe Ala Leu Asn Pro
        35                  40                  45

Gly Leu Leu Glu Thr Thr Glu Gly Cys Gln Gln Ile Met Arg Gln Leu
    50                  55                  60

Gln Pro Ala Leu Gln Thr
65                  70

<210> SEQ ID NO 105
<211> LENGTH: 70
<212> TYPE: PRT
<213> ORGANISM: Human immunodeficiency virus type 1

<400> SEQUENCE: 105

Met Gly Ala Arg Ala Ser Val Leu Ser Gly Gly Lys Leu Asp Glu Trp
 1               5                  10                  15

Glu Lys Ile Arg Leu Arg Pro Gly Gly Lys Lys Lys Tyr Arg Met Lys
            20                  25                  30

His Leu Val Trp Ala Ser Arg Glu Leu Glu Arg Phe Ala Leu Asn Pro
        35                  40                  45

Gly Leu Leu Glu Thr Thr Glu Gly Cys Gln Gln Ile Leu Gln Gln Leu
    50                  55                  60

Gln Pro Ala Leu Gln Thr
65                  70

<210> SEQ ID NO 106
<211> LENGTH: 70
<212> TYPE: PRT
<213> ORGANISM: Human immunodeficiency virus type 1

<400> SEQUENCE: 106

Met Gly Ala Arg Ala Ser Val Leu Ser Gly Gly Arg Leu Asp Ala Trp
 1               5                  10                  15

Glu Lys Ile Arg Leu Arg Pro Gly Gly Lys Lys Gln Tyr Arg Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Leu Gln Ile Ile Glu Gln Leu
    50                  55                  60

Gln Pro Ala Leu Lys Thr
65                  70

<210> SEQ ID NO 107
<211> LENGTH: 70
<212> TYPE: PRT
<213> ORGANISM: Human immunodeficiency virus type 1

<400> SEQUENCE: 107

Met Gly Ala Arg Ala Ser Val Leu Ser Gly Gly Lys Leu Asp Ala Trp
 1               5                  10                  15
```

-continued

Glu Lys Ile Arg Leu Arg Pro Gly Gly Lys Lys Tyr Arg Leu Lys
            20                  25                  30

His Leu Val Trp Ala Ser Arg Glu Leu Glu Arg Phe Ala Leu Asn Pro
                35                  40                  45

Asp Leu Leu Asp Thr Ala Glu Gly Cys Leu Gln Leu Ile Glu Gln Leu
    50                  55                  60

Gln Pro Ala Leu Lys Thr
 65              70

<210> SEQ ID NO 108
<211> LENGTH: 70
<212> TYPE: PRT
<213> ORGANISM: Human immunodeficiency virus type 1

<400> SEQUENCE: 108

Met Gly Ala Arg Ala Ser Val Leu Ser Gly Gly Lys Leu Asp Thr Trp
  1               5                  10                  15

Glu Lys Ile Arg Leu Arg Pro Gly Gly Ser Lys Lys Tyr Arg Leu Lys
            20                  25                  30

His Leu Val Trp Ala Ser Arg Glu Leu Glu Arg Phe Ala Leu Asn Pro
                35                  40                  45

Ser Leu Leu Glu Thr Thr Glu Gly Cys Arg Gln Ile Ile Arg Gln Leu
    50                  55                  60

Gln Pro Ser Leu Gln Thr
 65              70

<210> SEQ ID NO 109
<211> LENGTH: 70
<212> TYPE: PRT
<213> ORGANISM: Human immunodeficiency virus type 1

<400> SEQUENCE: 109

Met Gly Ala Ser Ala Ser Val Leu Thr Gly Ser Lys Leu Asp Ala Trp
  1               5                  10                  15

Glu Gln Ile Arg Leu Lys Pro Gly Ser Lys Lys Lys Tyr Arg Leu Lys
            20                  25                  30

His Leu Val Trp Ala Ser Arg Glu Leu Glu Arg Phe Ala Cys Asn Pro
                35                  40                  45

Glu Leu Leu Glu Thr Ala Glu Gly Asn Glu Lys Leu Leu Gln Gln Leu
    50                  55                  60

Glu Pro Ala Leu Lys Thr
 65              70

<210> SEQ ID NO 110
<211> LENGTH: 70
<212> TYPE: PRT
<213> ORGANISM: Human immunodeficiency virus type 1

<400> SEQUENCE: 110

Met Gly Ala Arg Ala Ser Val Leu Thr Gly Ser Lys Leu Asp Ala Trp
  1               5                  10                  15

Glu Arg Ile Arg Leu Arg Pro Gly Ser Lys Lys Ala Tyr Arg Leu Lys
            20                  25                  30

His Leu Val Trp Ala Ser Arg Glu Leu Glu Arg Tyr Ala Cys Asn Pro
                35                  40                  45

```
Gly Leu Leu Glu Thr Ala Glu Gly Thr Glu Gln Leu Leu Gln Gln Leu
    50                  55                  60

Glu Pro Ala Leu Lys Thr
 65                  70

<210> SEQ ID NO 111
<211> LENGTH: 70
<212> TYPE: PRT
<213> ORGANISM: Human immunodeficiency virus type 1

<400> SEQUENCE: 111

Met Gly Ala Arg Ala Ser Val Leu Thr Gly Gly Lys Leu Asp Arg Trp
  1               5                  10                  15

Glu Lys Val Arg Leu Arg Pro Gly Gly Arg Lys Arg Tyr Met Met Lys
                 20                  25                  30

His Leu Val Trp Ala Ser Arg Glu Leu Glu Arg Phe Ala Cys Asp Pro
            35                  40                  45

Gly Leu Met Glu Ser Lys Glu Gly Cys Thr Lys Leu Leu Gln Gln Leu
    50                  55                  60

Glu Pro Ala Leu Lys Thr
 65                  70

<210> SEQ ID NO 112
<211> LENGTH: 139
<212> TYPE: PRT
<213> ORGANISM: Human immunodeficiency virus type 2

<400> SEQUENCE: 112

Met Gly Ala Arg Asn Ser Val Leu Arg Gly Lys Lys Ala Asp Glu Leu
  1               5                  10                  15

Glu Arg Ile Arg Leu Arg Pro Gly Gly Lys Lys Lys Tyr Arg Leu Lys
                 20                  25                  30

His Ile Val Trp Ala Ala Asn Lys Leu Asp Arg Phe Gly Leu Ala Glu
            35                  40                  45

Ser Leu Leu Glu Ser Lys Glu Gly Cys Gln Lys Ile Leu Thr Val Leu
    50                  55                  60

Asp Pro Met Val Pro Thr Gly Ser Glu Asn Leu Lys Ser Leu Phe Asn
 65                  70                  75                  80

Thr Val Cys Val Ile Trp Cys Ile His Ala Glu Glu Lys Val Lys Asp
                 85                  90                  95

Thr Glu Gly Ala Lys Gln Ile Val Arg Arg His Leu Val Ala Glu Thr
            100                 105                 110

Gly Thr Ala Glu Lys Met Pro Ser Thr Ser Arg Pro Thr Ala Pro Ser
            115                 120                 125

Ser Glu Lys Gly Gly Asn Tyr Pro Val Gln His
        130                 135

<210> SEQ ID NO 113
<211> LENGTH: 137
<212> TYPE: PRT
<213> ORGANISM: Human immunodeficiency virus type 2

<400> SEQUENCE: 113

Met Gly Ala Arg Asn Ser Val Leu Arg Gly Lys Lys Ala Asp Glu Leu
  1               5                  10                  15

Glu Lys Ile Arg Leu Arg Pro Gly Gly Lys Lys Lys Tyr Lys Leu Lys
                 20                  25                  30
```

His Ile Val Trp Ala Ala Asn Glu Leu Asp Arg Phe Gly Leu Ala Glu
            35                  40                  45

Ser Leu Leu Glu Ser Lys Glu Gly Cys Gln Lys Ile Leu Thr Val Leu
    50                  55                  60

Asp Pro Leu Val Pro Thr Gly Ser Glu Asn Leu Lys Ser Leu Phe Asn
65                  70                  75                  80

Thr Val Cys Val Ile Trp Cys Ile His Ala Glu Glu Lys Val Lys Asp
                85                  90                  95

Thr Glu Gly Ala Lys Gln Ile Val Gln Arg His Leu Val Ala Glu Thr
                100                 105                 110

Gly Thr Ala Glu Lys Met Pro Asn Thr Ser Arg Pro Thr Ala Pro Pro
            115                 120                 125

Ser Gly Lys Asn Phe Pro Val Gln Gln
            130                 135

<210> SEQ ID NO 114
<211> LENGTH: 139
<212> TYPE: PRT
<213> ORGANISM: Human immunodeficiency virus type 2

<400> SEQUENCE: 114

Met Gly Ala Lys Asn Ser Val Leu Arg Gly Lys Lys Ala Asp Glu Leu
1               5                   10                  15

Glu Lys Ile Arg Leu Arg Pro Gly Gly Lys Lys Lys Tyr Arg Leu Lys
            20                  25                  30

His Ile Val Trp Ala Ala Asn Glu Leu Asp Arg Phe Gly Leu Thr Glu
            35                  40                  45

Ser Leu Leu Glu Ser Lys Glu Gly Cys Gln Lys Ile Ile Ser Val Leu
    50                  55                  60

Glu Pro Leu Val Pro Thr Gly Ser Glu Asn Leu Lys Ser Leu Tyr Asn
65                  70                  75                  80

Thr Thr Cys Val Ile Trp Cys Leu His Ala Glu Glu Lys Val Lys Asp
                85                  90                  95

Thr Glu Glu Ala Lys Arg Ile Val Gln Arg His Leu Val Ala Glu Thr
                100                 105                 110

Glu Thr Ala Glu Lys Met Pro Asn Ile Ser Arg Pro Thr Ala Pro Pro
            115                 120                 125

Ser Gly Lys Gly Gly Asn Phe Pro Val Gln Gln
            130                 135

<210> SEQ ID NO 115
<211> LENGTH: 139
<212> TYPE: PRT
<213> ORGANISM: Human immunodeficiency virus type 2

<400> SEQUENCE: 115

Met Gly Ala Arg Asn Ser Val Leu Arg Gly Lys Lys Ala Asp Glu Leu
1               5                   10                  15

Glu Lys Ile Arg Leu Arg Pro Gly Gly Lys Lys Lys Tyr Arg Leu Lys
            20                  25                  30

His Ile Val Trp Ala Ala Asn Glu Leu Asp Arg Phe Gly Leu Ala Glu
            35                  40                  45

Ser Leu Leu Glu Ser Lys Glu Gly Cys Gln Lys Ile Leu Thr Val Leu
    50                  55                  60

Asp Pro Leu Val Pro Thr Gly Ser Glu Asn Leu Lys Ser Leu Phe Asn
65                  70                  75                  80

```
Thr Val Cys Val Ile Trp Cys Ile His Ala Glu Glu Lys Ala Lys Asp
                85                  90                  95

Thr Glu Glu Ala Lys Gln Lys Val Gln Arg His Leu Val Ala Glu Thr
            100                 105                 110

Lys Thr Thr Glu Lys Met Pro Ser Thr Ser Arg Pro Thr Ala Pro Pro
        115                 120                 125

Ser Gly Asn Gly Gly Asn Phe Pro Val Gln Gln
    130                 135
```

<210> SEQ ID NO 116
<211> LENGTH: 139
<212> TYPE: PRT
<213> ORGANISM: Human immunodeficiency virus type 2

<400> SEQUENCE: 116

```
Met Gly Ala Arg Asn Ser Val Leu Arg Gly Lys Lys Ala Asp Glu Leu
 1               5                  10                  15

Glu Lys Val Arg Leu Arg Pro Gly Gly Lys Lys Lys Tyr Arg Leu Lys
            20                  25                  30

His Ile Val Trp Ala Ala Asn Glu Leu Asp Lys Phe Gly Leu Ala Glu
        35                  40                  45

Ser Leu Leu Glu Ser Lys Glu Gly Cys Gln Lys Ile Leu Arg Val Leu
    50                  55                  60

Asp Pro Leu Val Pro Thr Gly Ser Glu Asn Leu Lys Ser Leu Phe Asn
65                  70                  75                  80

Thr Val Cys Val Ile Trp Cys Leu His Ala Glu Lys Val Lys Asp
                85                  90                  95

Thr Glu Glu Ala Lys Lys Leu Ala Gln Arg His Leu Val Ala Glu Thr
            100                 105                 110

Gly Thr Ala Glu Lys Met Pro Asn Thr Ser Arg Pro Thr Ala Pro Pro
        115                 120                 125

Ser Gly Lys Arg Gly Asn Tyr Pro Val Gln Gln
    130                 135
```

<210> SEQ ID NO 117
<211> LENGTH: 139
<212> TYPE: PRT
<213> ORGANISM: Human immunodeficiency virus type 2

<400> SEQUENCE: 117

```
Met Gly Ala Arg Asn Ser Val Leu Arg Gly Lys Lys Ala Asp Glu Leu
 1               5                  10                  15

Glu Lys Val Arg Leu Arg Pro Gly Gly Lys Lys Lys Tyr Lys Leu Lys
            20                  25                  30

His Ile Val Trp Ala Ala Asn Glu Leu Asp Arg Phe Gly Leu Ala Glu
        35                  40                  45

Ser Leu Leu Glu Ser Lys Glu Gly Cys Gln Arg Ile Leu Lys Val Leu
    50                  55                  60

Asp Pro Leu Val Pro Thr Gly Ser Glu Asn Leu Lys Ser Leu Phe Asn
65                  70                  75                  80

Thr Val Cys Val Ile Trp Cys Ile His Ala Glu Glu Lys Val Lys Asp
                85                  90                  95

Thr Glu Glu Ala Lys Arg Ile Ala Leu Arg His Leu Ala Ala Glu Thr
            100                 105                 110

Gly Thr Ala Glu Lys Met Pro Asp Thr Ser Arg Pro Thr Ala Pro Pro
        115                 120                 125
```

```
Ser Gly Lys Gly Gly Asn Tyr Pro Val Gln Ser
    130                 135
```

<210> SEQ ID NO 118
<211> LENGTH: 139
<212> TYPE: PRT
<213> ORGANISM: Human immunodeficiency virus type 2

<400> SEQUENCE: 118

```
Met Gly Ala Arg Asn Ser Val Leu Arg Gly Lys Lys Ala Asp Glu Leu
 1               5                  10                  15

Glu Lys Val Arg Leu Arg Pro Asn Gly Lys Lys Arg Tyr Arg Leu Lys
             20                  25                  30

His Val Val Trp Ala Ala Asn Glu Leu Asp Arg Phe Gly Leu Ala Glu
         35                  40                  45

Ser Leu Leu Glu Ser Lys Glu Gly Cys Gln Lys Ile Leu Lys Val Leu
     50                  55                  60

Glu Pro Leu Val Pro Thr Gly Ser Glu Asn Leu Lys Ser Leu Phe Asn
 65                  70                  75                  80

Thr Val Cys Val Ile Trp Cys Leu His Ala Glu Lys Val Lys Asp
                 85                  90                  95

Thr Glu Glu Ala Lys Lys Leu Ala Gln Arg His Leu Val Ala Glu Thr
                100                 105                 110

Gly Thr Ala Glu Lys Met Pro Asn Ile Ser Arg Pro Thr Ala Pro Pro
            115                 120                 125

Ser Gly Lys Gly Gly Asn Phe Pro Val Gln Gln
    130                 135
```

<210> SEQ ID NO 119
<211> LENGTH: 140
<212> TYPE: PRT
<213> ORGANISM: Human immunodeficiency virus type 2

<400> SEQUENCE: 119

```
Met Gly Ala Arg Asn Ser Val Leu Arg Gly Lys Lys Ala Asp Glu Leu
 1               5                  10                  15

Glu Lys Ile Arg Leu Arg Pro Ser Gly Lys Lys Lys Tyr Arg Leu Lys
             20                  25                  30

His Ile Val Trp Ala Ala Asn Glu Leu Asp Arg Phe Gly Leu Ala Glu
         35                  40                  45

Ser Leu Leu Glu Ser Lys Glu Gly Cys Gln Lys Ile Leu Thr Val Leu
     50                  55                  60

Asp Pro Leu Val Pro Thr Gly Ser Glu Asn Leu Lys Ser Leu Phe Asn
 65                  70                  75                  80

Thr Val Cys Val Ile Trp Cys Leu His Ala Glu Glu Lys Val Lys Asp
                 85                  90                  95

Thr Glu Glu Ala Lys Lys Leu Val Gln Arg His Leu Gly Ala Glu Thr
                100                 105                 110

Gly Thr Ala Glu Lys Met Pro Ser Thr Ser Arg Pro Thr Ala Pro Pro
            115                 120                 125

Ser Gly Arg Gly Arg Asn Phe Pro Val Gln Gln Thr
    130                 135                 140
```

<210> SEQ ID NO 120
<211> LENGTH: 134
<212> TYPE: PRT
<213> ORGANISM: Human immunodeficiency virus type 2

```
<400> SEQUENCE: 120

Met Gly Ala Arg Gly Ser Val Leu Ser Gly Lys Lys Thr Asp Glu Leu
1               5                   10                  15

Glu Lys Val Arg Leu Arg Pro Gly Gly Lys Lys Tyr Met Leu Lys
                20                  25                  30

His Val Val Trp Ala Val Asn Glu Leu Asp Arg Phe Gly Leu Ala Glu
                35                  40                  45

Ser Leu Leu Glu Ser Lys Glu Gly Cys Gln Lys Ile Leu Lys Val Leu
        50                  55                  60

Ala Pro Leu Val Pro Thr Gly Ser Glu Asn Leu Lys Ser Leu Phe Asn
65                  70                  75                  80

Ile Val Cys Val Ile Phe Cys Leu His Ala Glu Glu Lys Val Lys Asp
                85                  90                  95

Thr Glu Glu Ala Lys Lys Ile Ala Gln Arg His Leu Ala Ala Asp Thr
                100                 105                 110

Glu Lys Met Pro Ala Thr Asn Lys Pro Thr Ala Pro Pro Ser Gly Gly
                115                 120                 125

Asn Tyr Pro Val Gln Gln
        130

<210> SEQ ID NO 121
<211> LENGTH: 134
<212> TYPE: PRT
<213> ORGANISM: Human immunodeficiency virus type 2

<400> SEQUENCE: 121

Met Gly Ala Arg Ser Ser Val Leu Ser Gly Lys Lys Thr Asp Glu Leu
1               5                   10                  15

Glu Lys Val Arg Leu Arg Pro Gly Gly Lys Lys Arg Tyr Cys Leu Lys
                20                  25                  30

His Ile Ile Trp Ala Val Asn Glu Leu Asp Arg Phe Gly Leu Ala Glu
                35                  40                  45

Ser Leu Leu Glu Ser Lys Glu Gly Cys His Lys Ile Leu Thr Val Leu
        50                  55                  60

Ala Pro Leu Val Pro Thr Gly Ser Glu Asn Leu Lys Ser Leu Phe Asn
65                  70                  75                  80

Thr Val Cys Val Ile Tyr Cys Leu His Ala Glu Glu Lys Val Lys Asp
                85                  90                  95

Thr Glu Glu Ala Lys Lys Ile Ala Gln Arg His Leu Ala Ala Asp Thr
                100                 105                 110

Glu Lys Met Pro Ala Thr Ser Arg Pro Thr Ala Pro Pro Ser Gly Gly
                115                 120                 125

Asn Tyr Pro Val Gln Gln
        130

<210> SEQ ID NO 122
<211> LENGTH: 139
<212> TYPE: PRT
<213> ORGANISM: Human immunodeficiency virus type 2

<400> SEQUENCE: 122

Met Gly Ala Arg Asn Ser Val Leu Ser Gly Lys Lys Ala Asp Glu Leu
1               5                   10                  15

Glu Lys Ile Arg Leu Arg Pro Gly Gly Lys Lys Lys Tyr Met Leu Lys
                20                  25                  30
```

```
His Val Val Trp Ala Ala Asn Glu Leu Asp Arg Phe Gly Leu Ala Glu
            35                  40                  45

Ser Leu Leu Glu Asn Lys Glu Gly Cys Gln Lys Ile Leu Ser Val Leu
 50                      55                  60

Ala Pro Leu Val Pro Thr Gly Ser Glu Asn Leu Lys Ser Leu Tyr Asn
 65                  70                  75                  80

Thr Val Cys Val Ile Trp Cys Ile His Ala Glu Glu Lys Val Lys His
                85                  90                  95

Thr Glu Glu Ala Lys Gln Ile Val Gln Arg His Leu Val Val Glu Thr
                100                 105                 110

Gly Thr Ala Glu Thr Met Pro Lys Thr Ser Arg Pro Thr Ala Pro Ser
            115                 120                 125

Ser Gly Arg Gly Gly Asn Tyr Pro Val Gln Gln
    130                 135

<210> SEQ ID NO 123
<211> LENGTH: 139
<212> TYPE: PRT
<213> ORGANISM: Human immunodeficiency virus type 2

<400> SEQUENCE: 123

Met Gly Ala Arg Asn Ser Val Leu Ser Gly Lys Lys Ala Asp Glu Leu
 1               5                  10                  15

Glu Lys Ile Arg Leu Arg Pro Gly Gly Lys Lys Lys Tyr Met Leu Lys
                20                  25                  30

His Val Val Trp Ala Ala Asn Glu Leu Asp Arg Phe Gly Leu Ala Glu
            35                  40                  45

Ser Leu Leu Glu Asn Lys Glu Gly Cys Gln Lys Ile Leu Ser Val Leu
 50                      55                  60

Ala Pro Leu Val Pro Thr Gly Ser Glu Asn Leu Lys Ser Leu Tyr Asn
 65                  70                  75                  80

Thr Val Cys Val Ile Trp Cys Ile His Ala Glu Glu Lys Val Lys His
                85                  90                  95

Thr Glu Glu Ala Lys Gln Ile Val Gln Arg His Leu Val Val Glu Thr
                100                 105                 110

Gly Thr Ala Glu Thr Met Pro Lys Thr Ser Arg Pro Thr Ala Pro Ser
            115                 120                 125

Ser Gly Arg Gly Gly Asn Tyr Pro Val Gln Gln
    130                 135

<210> SEQ ID NO 124
<211> LENGTH: 139
<212> TYPE: PRT
<213> ORGANISM: Human immunodeficiency virus type 2

<400> SEQUENCE: 124

Met Gly Ala Arg Asn Ser Val Leu Ser Gly Lys Lys Ala Asp Glu Leu
 1               5                  10                  15

Glu Lys Ile Arg Leu Arg Pro Asn Gly Lys Lys Lys Tyr Met Leu Lys
                20                  25                  30

His Val Val Trp Ala Ala Asn Glu Leu Asp Arg Phe Gly Leu Ala Glu
            35                  40                  45

Ser Leu Leu Glu Asn Lys Glu Gly Cys Gln Lys Ile Leu Ser Val Leu
 50                      55                  60

Ala Pro Leu Val Pro Thr Gly Ser Glu Asn Leu Lys Ser Leu Tyr Asn
 65                  70                  75                  80
```

```
Thr Val Cys Val Ile Trp Cys Ile His Ala Glu Glu Lys Val Lys His
                85                  90                  95

Thr Glu Glu Ala Lys Gln Ile Val Gln Arg His Leu Val Val Glu Thr
            100                 105                 110

Gly Thr Ala Glu Ile Met Pro Lys Thr Ser Arg Pro Thr Ala Pro Ser
            115                 120                 125

Ser Gly Arg Gly Gly Asn Tyr Pro Val Gln Gln
            130                 135
```

<210> SEQ ID NO 125
<211> LENGTH: 139
<212> TYPE: PRT
<213> ORGANISM: Human immunodeficiency virus type 2

<400> SEQUENCE: 125

```
Met Gly Ala Arg Asn Ser Val Leu Ser Gly Lys Lys Ala Asp Glu Leu
  1               5                  10                  15

Glu Lys Ile Arg Leu Arg Pro Gly Gly Lys Lys Lys Tyr Met Leu Lys
                 20                  25                  30

His Val Val Trp Ala Ala Asn Glu Leu Asp Arg Phe Gly Leu Ala Glu
             35                  40                  45

Ser Leu Leu Glu Asn Lys Glu Gly Cys Gln Lys Ile Leu Ser Val Leu
    50                  55                  60

Ala Pro Leu Val Pro Thr Gly Ser Glu Asn Leu Lys Ser Leu Tyr Asn
 65                  70                  75                  80

Thr Val Cys Val Ile Trp Cys Ile His Ala Glu Glu Lys Val Lys His
                85                  90                  95

Thr Glu Glu Ala Lys Gln Ile Val Gln Arg His Leu Val Met Glu Thr
            100                 105                 110

Gly Thr Ala Glu Thr Met Pro Lys Thr Ser Arg Pro Thr Ala Pro Phe
            115                 120                 125

Ser Gly Arg Gly Gly Asn Tyr Pro Val Gln Gln
            130                 135
```

<210> SEQ ID NO 126
<211> LENGTH: 139
<212> TYPE: PRT
<213> ORGANISM: Human immunodeficiency virus type 2

<400> SEQUENCE: 126

```
Met Gly Val Arg Asn Ser Val Leu Ser Gly Lys Lys Ala Asp Glu Leu
  1               5                  10                  15

Glu Lys Ile Arg Leu Arg Pro Asn Gly Lys Lys Lys Tyr Met Leu Lys
                 20                  25                  30

His Val Val Trp Ala Ala Asn Glu Leu Asp Arg Phe Gly Leu Ala Glu
             35                  40                  45

Ser Leu Leu Glu Asn Lys Glu Gly Cys Gln Lys Ile Leu Ser Val Leu
    50                  55                  60

Ala Pro Leu Val Pro Thr Gly Ser Glu Asn Leu Lys Ser Leu Tyr Asn
 65                  70                  75                  80

Thr Val Cys Val Ile Trp Cys Ile His Ala Glu Glu Lys Val Lys His
                85                  90                  95

Thr Glu Glu Ala Lys Gln Ile Val Gln Arg His Leu Val Val Glu Thr
            100                 105                 110

Gly Thr Thr Glu Thr Met Pro Lys Thr Ser Arg Pro Thr Ala Pro Ser
            115                 120                 125
```

Ser Gly Arg Gly Gly Asn Tyr Pro Val Gln Gln
    130                 135

<210> SEQ ID NO 127
<211> LENGTH: 139
<212> TYPE: PRT
<213> ORGANISM: Human immunodeficiency virus type 2

<400> SEQUENCE: 127

Met Gly Ala Arg Asn Ser Val Leu Ser Gly Lys Lys Ala Asp Glu Leu
 1               5                  10                  15

Glu Lys Ile Arg Leu Arg Pro Gly Gly Lys Lys Lys Tyr Met Leu Lys
            20                  25                  30

His Val Val Trp Ala Ala Asn Glu Leu Asp Arg Phe Gly Leu Ala Glu
        35                  40                  45

Ser Leu Leu Glu Asn Lys Glu Gly Cys Gln Lys Ile Leu Ser Val Leu
    50                  55                  60

Ala Pro Leu Val Pro Thr Gly Ser Glu Asn Leu Lys Ser Leu Tyr Asn
65                  70                  75                  80

Thr Val Cys Val Ile Trp Cys Ile His Ala Glu Glu Lys Val Lys His
                85                  90                  95

Thr Glu Glu Ala Lys Gln Ile Val Gln Arg His Leu Val Val Glu Thr
            100                 105                 110

Gly Thr Ala Glu Thr Met Pro Lys Thr Ser Arg Pro Thr Ala Pro Ser
        115                 120                 125

Ser Gly Arg Gly Gly Asn Tyr Pro Val Gln Gln
    130                 135

<210> SEQ ID NO 128
<211> LENGTH: 139
<212> TYPE: PRT
<213> ORGANISM: Human immunodeficiency virus type 2

<400> SEQUENCE: 128

Met Gly Ala Arg Asn Ser Val Leu Ser Gly Lys Glu Ala Asp Glu Leu
 1               5                  10                  15

Glu Lys Val Arg Leu Arg Pro Asn Gly Lys Lys Lys Tyr Met Leu Lys
            20                  25                  30

His Val Val Trp Ala Ala Asn Glu Leu Asp Arg Phe Gly Leu Ala Glu
        35                  40                  45

Ser Leu Leu Asp Asn Lys Glu Gly Cys Gln Lys Ile Leu Ser Val Leu
    50                  55                  60

Ala Pro Leu Val Pro Thr Gly Ser Glu Asn Leu Lys Ser Leu Tyr Asn
65                  70                  75                  80

Thr Val Cys Val Ile Trp Cys Ile His Ala Glu Glu Lys Val Lys His
                85                  90                  95

Thr Glu Glu Ala Lys Gln Ile Val Gln Arg His Leu Val Val Glu Thr
            100                 105                 110

Gly Thr Ala Asp Arg Met Pro Ala Thr Ser Arg Pro Thr Ala Pro Pro
        115                 120                 125

Ser Gly Arg Gly Gly Asn Tyr Pro Val Gln Gln
    130                 135

<210> SEQ ID NO 129
<211> LENGTH: 139
<212> TYPE: PRT
<213> ORGANISM: Human immunodeficiency virus type 2

```
<400> SEQUENCE: 129

Met Gly Val Arg Asn Ser Val Leu Ser Gly Lys Lys Ala Asp Glu Leu
  1               5                  10                  15

Glu Lys Ile Arg Leu Arg Pro Gly Gly Lys Lys Tyr Met Leu Lys
             20                  25                  30

His Ile Val Trp Ala Ala Asn Glu Leu Asp Arg Phe Gly Leu Ala Glu
             35                  40                  45

Ser Leu Leu Glu Asn Lys Glu Gly Cys Gln Lys Ile Leu Ser Val Leu
 50                  55                  60

Ala Pro Leu Val Pro Thr Gly Ser Glu Asn Leu Lys Ser Leu Tyr Asn
 65                  70                  75                  80

Thr Val Arg Val Leu Trp Cys Ile His Ala Glu Glu Lys Val Lys His
                 85                  90                  95

Thr Glu Glu Ala Lys Gln Ile Val Gln Arg His Leu Val Val Glu Thr
                100                 105                 110

Gly Thr Ala Asp Lys Met Pro Ala Thr Ser Arg Pro Thr Ala Pro Pro
            115                 120                 125

Ser Gly Arg Gly Gly Asn Tyr Pro Val Gln Gln
        130                 135

<210> SEQ ID NO 130
<211> LENGTH: 139
<212> TYPE: PRT
<213> ORGANISM: Human immunodeficiency virus type 2

<400> SEQUENCE: 130

Met Gly Ala Arg Asn Ser Val Leu Ser Gly Lys Lys Ala Asp Glu Leu
  1               5                  10                  15

Glu Lys Ile Arg Leu Arg Pro Gly Gly Lys Lys Arg Tyr Gln Leu Lys
             20                  25                  30

His Ile Val Trp Ala Ala Asn Glu Leu Asp Arg Phe Gly Leu Ala Glu
             35                  40                  45

Ser Leu Leu Glu Asn Lys Glu Gly Cys Gln Lys Ile Leu Ser Val Leu
 50                  55                  60

Ala Pro Leu Val Pro Thr Gly Ser Glu Asn Leu Lys Ser Leu Tyr Asn
 65                  70                  75                  80

Thr Val Cys Val Leu Trp Cys Ile His Ala Glu Glu Lys Val Lys His
                 85                  90                  95

Thr Glu Glu Ala Lys Gln Ile Val Gln Arg His Leu Val Val Glu Thr
                100                 105                 110

Gly Thr Ala Asp Lys Met Pro Ala Thr Ser Arg Pro Thr Ala Pro Pro
            115                 120                 125

Ser Gly Lys Gly Gly Asn Tyr Pro Val Gln Gln
        130                 135

<210> SEQ ID NO 131
<211> LENGTH: 139
<212> TYPE: PRT
<213> ORGANISM: Human immunodeficiency virus type 2

<400> SEQUENCE: 131

Met Gly Ala Arg Ser Ser Val Leu Ser Gly Lys Lys Ala Asp Glu Leu
  1               5                  10                  15

Glu Lys Val Arg Leu Arg Pro Gly Gly Lys Lys Tyr Met Leu Lys
             20                  25                  30
```

-continued

```
His Val Val Trp Ala Ala Asn Glu Leu Asp Arg Phe Gly Leu Ala Glu
        35              40                  45

Ser Leu Leu Glu Ser Lys Glu Gly Cys Gln Lys Ile Ile Thr Val Leu
        50              55                  60

Glu Pro Leu Val Pro Thr Gly Ser Glu Asn Leu Lys Ser Leu Phe Asn
65              70                  75                      80

Thr Val Cys Val Ile Trp Cys Ile His Ala Glu Glu Lys Val Lys His
            85                  90                      95

Thr Glu Glu Ala Lys Gln Val Val Lys Arg His Leu Val Val Glu Thr
            100                 105                 110

Gly Thr Ala Asn Lys Met Pro Ala Thr Ser Arg Pro Thr Ala Pro Pro
        115             120                 125

Ser Gly Arg Gly Gly Asn Tyr Pro Val Gln Gln
130                 135
```

ANTI-HIV PEPTIDES AND PROTEINS

The present application is a 371 national phase application of PCT/GB98/00563.

This invention relates to novel peptides and proteins useful against HIV infection, in particular, peptides and proteins which are derived from HIV p17 or p16 matrix proteins. The invention also relates to nucleic acids encoding the peptides and proteins and vectors containing the nucleic acids, in particular delivery vectors useful in gene therapy, such as retroviral vectors. The invention further relates to uses of the nucleic acids and vectors in gene therapy.

Despite intensive research efforts, there has been limited success in the development of low molecular weight compounds as treatments for HIV infection and AIDS. Similarly, it seems unlikely that a protective or therapeutic vaccine will be produced in the near future. This situation has led to recent proposals that greater emphasis should be given to biological therapeutics (Lehrman, 1994) and there is currently much interest in the prospect of gene therapy as a clinical approach to HIV-1 infection. Several molecules have been proposed as anti-HIV therapeutics, including ribozymes, trans-dominant proteins, scFv molecules, antisense constructs and TAR and RRE decoys (reviewed in Yu et al 1994). These molecules are envisaged to act both as therapy against already infected cells and as protective 'intracellular immunisation' (Baltimore, 1988) in uninfected cells. In addition, the use of toxins (suicide genes) or immunological markers has also been proposed as a means of killing infected cells so reducing the viral load in the patient.

Human immunodeficiency virus (HIV-1) has two genes that encode the structural proteins of the virus, these are the gag and env genes. The gag gene codes for a precursor protein call Gag or p55 which is proteolytically processed to produce the matrix protein (p17), the capsid protein (p24), the nucleocapsid protein (p7) and an additional protein, p6. Together these Gag derived proteins form the core of the virus particle. The correct functioning of these components is critical for viral particle production and infectivity.

The P17 protein forms the amino terminus of both the precursor Gag poly-protein p55$^{gag}$, and p160$^{gag-pol}$. Following proteolytic cleavage during particle maturation the p17 protein assembles into a shell referred to as the matrix (MA) directly underneath the lipid membrane. P17 pays a pivotal role at two stages in the life cycle of HIV-1. Late in infection it directs the precursor Gag polypeptide to the plasma membrane where assembly and budding occur (Gelderblom 1991) and early in a new infection it plays a role in penetration and uncoating (Yu et al 1992) and in mediating the nuclear transport of pre-integration complexes (Bukrinskaya et al 1996). The three dimensional structure of p17 has been determined and the protein is known to form a trimer which then assembles into the higher order structure of the viral core (Nermut et al 1994). The globular central core of the protein forms a compact fold consisting of four helices, with striking structural homology to IFNγ. In addition, the protein contains a highly basic platform consisting of three β-strands.

A classical approach to inhibiting viral replication is to block the assembly of the viral components into virus particles by providing an excess of a mutant form of the normal viral proteins, the mutant protein is referred to as a trans-dominant inhibitor. It is generally thought that the mutant protein interferes with critical protein to protein interactions that are required to build up the structure of the viral particle. However other mechanisms can be envisaged such as the interference with cellular factors, such as the cyclophilins (Luban et al 1993) or protein kinases (Yu et al 1995) that might be required for proper virus particle formation. The approach was first proposed as a strategy for blocking HIV replication by Baltimore (1988) who subsequently demonstrated that the expression of a truncated form of one of the Gag proteins, p24, reduced viral replication (Trono et al 1989). This general approach has been developed by others (e.g. Lee and Linial 1995; Neidrig et al 1995; Lori et al 1994; Smythe et al 1994; Karacostas et al 1993) and is reviewed by Modrow et al 1994 & Meile and Lever (1996). The approach is however not always successful. For example Miele and Lever (1996) failed to protect cells against infection by using a modified p55. In addition the expression of full length proteins may be toxic as observed for p55 (Miele and Modrow op. cit.) or have other effects such as inhibition of lymphocyte proliferation as observed for wild type p17 (Hofman et al 1994). In addition in some cases the inhibition of viral replication by trans-dominant mutants of Gag was not dramatic. For example a truncated form of p24 was poorly effective in one study (Lori et al 1994). There is therefore a need for more effective inhibitors of viral assembly. There is also a need for inhibitors which are non-toxic or have acceptably low toxicity.

The present invention shows how to disrupt the function of the matrix protein p17, of HIV-1 and its counterpart p16 in HIV-2. We have identified novel molecules derived from the HIV-1 and HIV-2 Gag proteins, p17 and p$^{16}$, that are potent inhibitors of viral replication. A first type of inhibitor comprises short peptides corresponding to part of the p17 or p16 protein and a second type of inhibitor comprises specific mutant forms of p17 or p16. The ability of these specific variants to inhibit HIV replication was not predicted.

The invention therefore provides in one aspect a peptide comprising an amino acid sequence of a part of the p17 protein of HIV-1 or of the p16 protein of HIV-2, from amino acid residues 31 to 45 or from amino acid residues 41 to 55 or a functional portion thereof, of which one or more residues may be conservatively substituted, said peptide capable of interfering with HIV replication.

In another aspect the invention provides a nucleic acid comprising at least one sequence encoding a peptide capable of interfering with HIV replication, which peptide comprises an amino acid sequence of a part of the p17 protein of HIV-1 or of the p16 protein of HIV-2, from amino acid residues :31 to 45 or a functional portion thereof, of which one or more residues may be conservatively substituted.

In another aspect the invention provides a nucleic acid comprising at least one sequence encoding a peptide capable of interfering with HIV replication, which peptide comprises an amino acid sequence of a part of the p17 protein of HIV-1 or of the p16 protein of HIV-2, from amino acid residues 41 to 55 or a functional portion thereof, of which one or more residues may be conservatively substituted.

Preferred peptides according to the invention are peptide 1 and peptide 2 designated by amino acid residues 31 to 45 and 41 to 55, respectively; and which may have conservative variations, in particular amino acid substitutions which do not significantly alter the characteristics of the peptide. Peptides 1 and 2 corresponding to the p17 amino acid sequence of the HXB2 HIV-2 isolate shown in FIG. 2 are:

Peptide 1: LKHIVWASRELERFA [SEQ ID NO: 1]

Peptide 2: LERFAVNPGLLETSE [SEQ ID NO: 2].

FIGS. 6 and 7 show p17 and p16 from a range of isolates of HIV-1 and HIV-:2, indicating the locations of peptides 1 and 2 according to the invention, within those isolates.

However, it will be evident that functional peptides may still be obtained by reducing the length of the two regions defined herein as p17 and p16 residues 31 to 45 and 41 to 55. Also, it may be possible to retain the functions of peptides 1 and 2 using longer amino acid sequences containing one or more residues extending at either or both ends of the peptides. Such shorter or longer amino acid sequences can easily be defined by known methods and are included within the scope of the invention.

Peptides according to the invention can range in length e.g. from 5 to 30 amino acids or longer, or preferably 6 to 20 amino acids. 6 amino acid residues is generally the shortest length for an epitope of reasonable specificity.

It will also be evident that regions of p17 and p16 corresponding to amino add residues 31 to 45 and 41 to 55 as described herein, may be found to have gaps or insertions in certain other HIV-1 and HIV-2 isolates and therefore not correspond precisely to the amino acid residue numbering given herein. However, it will always be possible for a person skilled in the art to identify the relevant regions. Thus, these possibilities are not excluded from the scope of the invention. A useful source of known HIV sequences is the Los Alamos Database (1993) "Human Retroviruses and AIDS—a compilation and analysis of nucleic acid and amino acid sequences".

In one embodiment, the invention provides a nucleic acid further comprising a sequence encoding a second peptide as described herein. More than two peptides may be encoded by the same nucleic acid according to the invention. The peptides may be all of the peptide 1 or all of the peptide 2 type, thus providing a homopolymer of peptides, or they may include a mixture of peptides in heteropolymer.

A peptide or peptides according to the invention may also be linked to an unrelated (i.e. non- p17 or p16) peptide or protein. The purpose may be for example to provide a combination trans-dominant inhibitor which comprises two or more inhibitors which act on different parts of the HIV life-cycle. Another reason for linking a peptide according to the invention to an unrelated molecule would be to stabilise the peptide in the cell in which it is expressed. For example, linking to the LacZ protein would provide stabilisation. Suitable linkers described herein in detail for linking two or more peptides according to the invention are also suitable for linking the peptides with unrelated molecules.

In another aspect, the invention provides a recombinant p17 or p16 protein which is incapable of functioning as the natural protein as a result of an alteration in helix A which is defined by nucleic acid residues 31 to 46, or the A-B loop which is defined by amino acid residues 47 to 52.

In another aspect, the invention provides a nucleic acid encodinig a recombinant protein as described herein.

Three specific embodiments of this aspect of the invention are described herein, namely substitution of amino acid residue A45, for example with I (iso-leucine); substitution of amino acid residue V46, for example with E (glutamic acid); and substitution of both R39 and R43, for example with E in both cases. It will be evident that the replacement amino acids in the three embodiments described are not limited to the examples given; any amino acid may be used which has the desired effect on the recombinant protein. Suitable amino acids will be recognisable to those skilled in the art, and can be tested using readily available techniques.

In further aspects, the invention provides vectors containing nucleic acids described herein. Such vectors include but are not limited to plasmids and retroviral vectors. Preferred vectors are gene delivery vectors. Suitable retroviral vectors for gene delivery are described in Cannon et al 1996 and WO 96/137623, incorporated herein by reference.

The invention also provides nucleic acids and vectors as described herein, for use in gene therapy; and the use of such nucleic acids and vectors in the manufacture of a medicament to reduce or inhibit HIV infection. For these embodiments, the nucleic acids and vectors may be supplied together with a pharmaceutically acceptable diluent or carrier.

The invention also provides peptides and recombinant proteins encoded by the nucleic acids and vectors described herein. The peptides and proteins may be supplied together with a pharmaceutically acceptable diluent or carrier, for administration to patients.

The invention is thus concerned with trans-dominant inhibitors, capable of interfering with HIV replication and thus infection. Trans-dominant inhibitors work by dominating the activity of a normal counterpart molecule, in this case p17 of HIV-1 or p16 of HIV-2. Effective trans-dominant inhibitors according to the invention will reduce viral load, preferably by at least 50%, and more preferably by 70% or more.

BRIEF DESCRIPTION OF THE DRAWINGS

FIG. 1 shows the nucleotide sequence (SEQ ID NO: 17) of the p17 coding region of HIV-1 strain pW13 (GenBank Accession No: K03455).

FIG. 4 is a nucleotide sequence containing an internal ribosome entry site (IRES), suitable for use in generating a polycistronic transcription unit encoding two or more p17 peptides as described herein.

Figure 2:
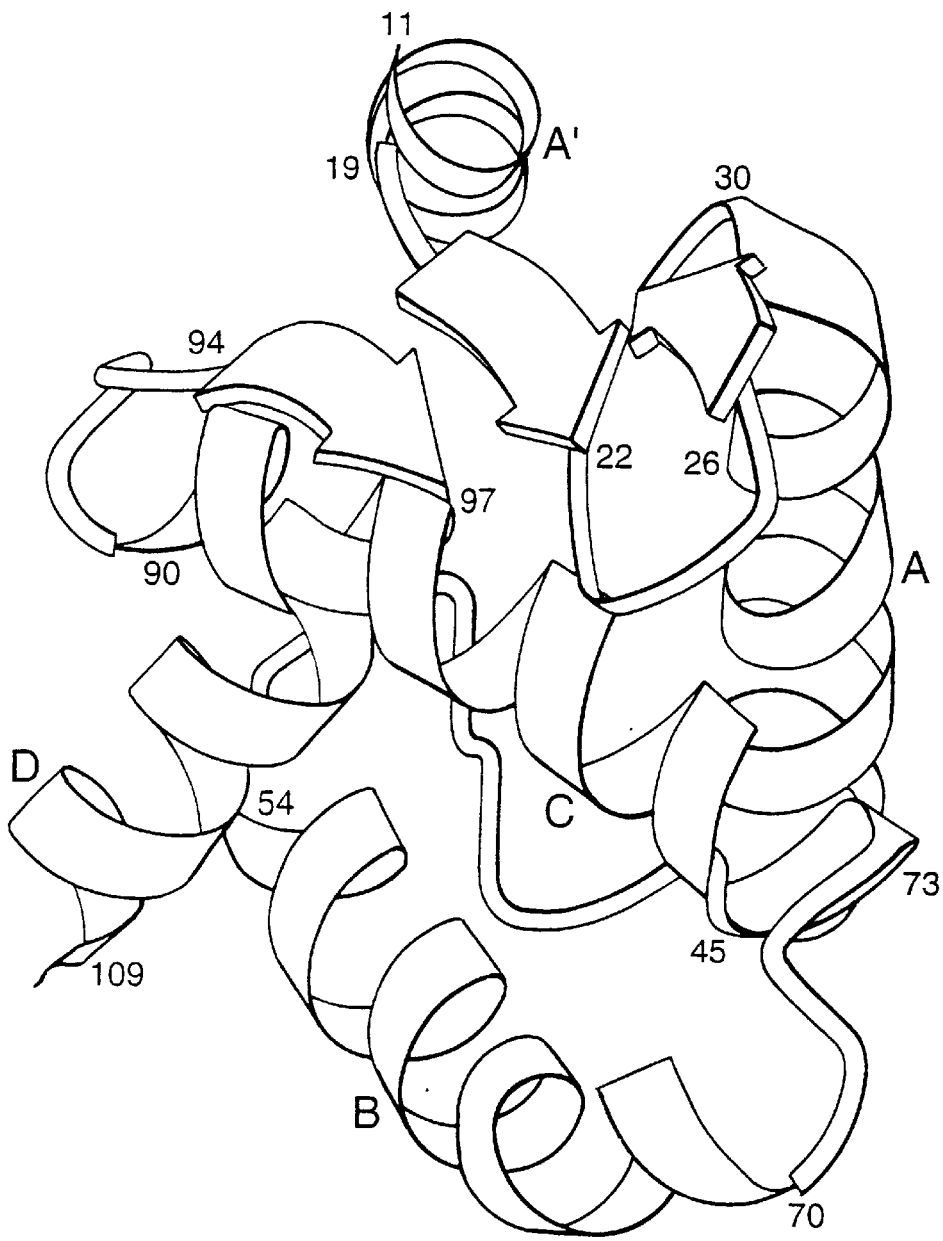
FIG. 2 shows the amino acid sequence (SEQ ID NO: 18) of p17, encoded by the nucleotide sequence of FIG. 1, together with the three dimensional structure of p17 (GenBank Accession No: K03455).

Table 3 shows p17 amino acid sequence alignments for different isolates of HIV-1. Table 4 shows amino acid sequence alignments for p16 of different isolates of HIV-2.

In Table 3, it can be seen that the peptides, and the specific sites of mutation for recombinant proteins disclosed herein, are found across a range of HIV-1 isolates.

R39 is invariant and is identifiable across strains as embedded at position 4 in consensus sequence B, 1-WASReLERFA-10 and R43 is identifiable at position 8. However in some variants e.g. HIVU455 there is a lysine (K) at this position. This is conservative variation and would be predicted to preserve the properties of p17 and to be disrupted by the mutations described herein.

The A45 position is highly conserved and is easily identified as residue 5 embedded in the sequence 1-LerFavnP-5 of consensus sequence B. In one case (HIVU455) there is a threonine at this residue. Conversion to an isoleucine (I) would be predicted to be disruptive in this strain.

The V46 residue is identified as being embedded within the sequence LerFavnP of consensus sequence B. This position is partially conserved in that in some strains there is a leucine (L), an isoleucine or a cysteine at this position. In all cases conversion to the charged residue glutamic acid (E) would be predicted to have a similar disruptive effect.

The start of Helix A is readily identified at the boundary of a charged region as marked. Peptide 1 is readily identified as marked. Peptide 2 is easily identified with a conserved giycine (G) at the C-terminal boundary.

A person ordinarily skilled in the analysis of protein structure could identify the peptides, regions and residues described for the HXB2 isolate herein, in any isolate of HIV-1.

Similarly, in Table 4 it can be seen that the same peptides, loop regions and residues described for the HIV-1 HXB2 isolate can be identified in HIV-2. p16 is the HIV-2 homologue of HIV-1 p17. Peptides 1 and 2 are identified in the table.

Peptide 1 is identified in the consensus sequence as LKH?vWAaNeLDrFG (SEQ ID NO: 19).

Peptide 2 is identified in the consensus sequence as LDrFGLaESLLesKEG (SEQ ID NO: 20).

R39E becomes N39E in HIV-2. R to N is not a conservative amino acid change but the specific mutation of N39 in p16 to eg. E would alter the charge density in this region and would therefore be predicted to have an effect as for mutation of R39 in p17.

A45I becomes G45I in HIV-2. A to G is a conservative change and the mutation of this residue in p16 to eg. I would have the same effect.

V46E becomes L46E in HIV-2. V to L is a conservative change and therefore the mutation is predicted to have the same effect in HIV-2.

Novel peptides with anti-HIV activity were discovered by screening an overlapping set of peptides derived from the p17 protein of HIV-1. Previous studies using this type of approach (Neidrig et al 1994) had revealed one inhibitory peptide spanning residues 47 to 59 but had found no activity in any other region. We screened smaller peptides and identified two inhibitory peptides (peptide 1 and peptide 2). Peptide 1 spans residues 31 to 45. Interestingly previous studies had shown that a peptide spanning residues 23 to 46 had no inhibitory activity (Neidrig et al 1994). Peptide 2 spanned residues 41 to 55. Part of this peptide overlaps that described previously (Neidrig et al op.cit.) however further analyses revealed that residues 45 and 46 are key functional sites in the protein and these are retained in our peptide 2.

Inhibitory proteins were discovered by making mutations in the p17 coding region of an infectious provirus and testing for the ability of the virus to produce infectious particles. For a mutant protein to have utility in gene therapy as an inhibitor of viral replication it must continue to be synthesised at normal or close to normal levels in the infected cell and retain some structural integrity to ensure that the appropriate protein interactions occur; however, the mutation must abolish the normal function of the protein. Of many mutations tested only three mutations fulfilled these criteria and are therefore predicted to function as trans-dominant inhibitors of viral replication. Interestingly these mutations are contained within the sequences of peptide 1 and peptide 2. By aligning peptide 1 and peptide 2 with the known structure of p17 (Mathews et al 1994; Massiah et al 1994) they were observed to encompass, respectively, an independently folded domain, helix A and an adjacent loop, the A-B loop. Our analysis of mutations in this region reveals that helix A is critical for viral replication. One mutation, R39E/R43E, produces large amounts of normally budded virus particles but these are non-infectious (Cannon et al 1997 op. cit.), a more disruptive mutation in this region has also been shown by others to have a similar phenotype (Reicin et al 1995). Two other mutations in the p17 coding region severely reduce viral replication. These are A45I and V46E which are located in the A-B loop and are adjacent to the inhibitory peptide described by Neidrig et al (1994). We consider, given this discovery that residues 45 and 46 are critical, that peptide 2 (41 to 55) constitutes a novel inhibitory peptide distinct from that described by Neidrig et al (1994) which did not contain these residues.

The present invention describes novel specific peptides and novel mutant proteins derived from the p17 protein and the p16 protein that can inhibit viral replication. It further describes a method for expressing the peptides or the mutant proteins in a retroviral vector. It describes the use of the retrovir vector to protect susceptible cells from HIV infection. The invention has application in gene therapy for AIDS.

DETAILS OF THE INVENTION

1. An analysis of the functional regions of the p17 protein.

The nucleic acid sequence of the p17 coding region of strain pWI3 (Kim et al 1989) is shown in FIG. 1. The corresponding amino acid sequence is shown in FIG. 2. The three dimensional structure of p17 is also shown in FIG. 2. The co-ordinates of key structural regions of p17 are taken from Mathews et al (1994) and Massiah et al (1994) and are noted in FIG. 2. They are, Helix A (residues L31 to V46), Helix B (residues T53 to Q69), Helix C (residues S72 to I92), Helix D (residues D96 to N109), A-B loop (residues 47 to 52). The amino acids are referred to by the standard single letter convention.

The methods used to construct and characterise variants of HIV1 that have one or more mutations in the coding region for p17 are given below. The details of the mutations and their phenotypes are summarised in Table 1.

Production of 17 mutant viruses

Single site mutations were introduced into the proviral clone WI3 (Kim et al 1989) using mismatched PCR primers extending from convenient restriction sites within the p17 coding sequence. All mutations were confirmed by sequencing the final reconstituted proviral DNA. Virus was generated by overnight calcium phosphate transfection of 293T cells as described (Cannon et al 1994). Cells were grown in DMEM supplemented with 10% FCS (GIBCO BRL) and transfected at 70% confluence with 30mg of plasmid DNA per 10 cm dish. Supernatants were harvested 48 hours post-transfection, clarified by centrifugation and filtered through 0.45 mm filters. Virus stocks were treated with DNAse I (Promega) for 1 hour at 37° C. in the presence of 6 mM $MgCl_2$ and stored in aliquots at −70° C. Virus production was measured by p24 ELISA (Coulter) or reverse transcriptase (RT) assay, using a Quant-T-RT kit (Amersham International).

Infectivity assays

Virus stocks were assayed for infectivity in the T cell line C8166. $5\times10^5$ cells were incubated in 1 ml of virus (approximately 500 ng p24) for 1 hour at 37° C. and then washed and plated in 2 ml fresh medium (RPMI, 10% FCS). Infectivity was scored 2–3 days later by the appearance of syncytia. Virus stocks were also used to infect the H9 T cell line. $3\times10^6$ cells were incubated with equal amounts of wild-type and mutant virus (as measured by RT activity) in a total volume of 1 ml for 1 hour and then washed and plated in 5 ml medium. Samples of the culture supernatant were taken every 3–4 days and assayed for RT activity to monitor virus production. Infectivity was also assayed using MAGI cells. Equivalent volumes of viral supematants from transient transfections of 293T cells were used to infect MAGI cells plated at 20% confluence in 24-well plates. The cells were stained for β-galactosidase activity 48 hours later as described (Kimpton et al, 1992) and the number of cells staining blue was determined by light microscopy. All infections were performed with at least two independently produced virus stocks for each mutant tested.

Analysis of viral proteins

Viral proteins were concentrated from the supernatants of transfected 293T cells by centrifugation through a 20% sucrose cushion at 50,000 rpm at 4° C. for 2 hours using a TL1 00.4 rotor. The pellets were resuspended in 40 ml loading buffer and stored at −70° C. Aliquots were heated to 90° C. for 5 minutes before analysis by SDS-PAGE. HIV-1 proteins were detected by Western blotting using pooled serum from HIV-1 -infected donors at 1:500 dilution. A specific anti-p17 monoclonal antibody (Capricorn, MA) was used at 1:500 dilution. The secondary antibodies used were horse radish peroxidase-conjugated goat anti-human immunoglobulin and goat anti-rabbit immunoglobulin (Vector), used at 1:1,000 and 1:4,000 dilutions respectively. Specific interactions were visualised by the ECL detection system (Amersham).

Electron microscopy

Transfected 293T cells were fixed in 2.5% glutaraldehyde, post-fixed in 1% osmium tetroxide in isotonic buffer and then treated with 0.5% aqueous uranyl acetate, dehydrated in ethanol and embedded via epoxy propane in Araldite resin. Sections were cut with a diamond knife, stained with uranyl acetate and lead citrate and examined with a Philips CM12 electron microscope.

Some mutations dramatically reduce viral infectivity. In some cases this is due to an effect on protein production and/or stability e.g. L50A, L51A, C75S and Y86R, C87S. One mutation, R39E/R43E is particularly interesting in that levels of viral protein and particles is unaffected but the resulting virus is virtually non-infectious. This double mutation causes particles to become re-located to the cytoplasm. A previously described mutation, R42A, only modestly altered the kinetics of viral replication (Massiah et al 1994; table 4) emphasising the fact that the specific phenotype of changes at particular residues cannot necessarily be predicted. Two other mutations that we produced, A45I and V46E have no effect on particle formation or location in the cell yet viral infectivity is significantly reduced.

The structure of the R39E/R43E, A45I and V46E mutated proteins was determined by nuclear magnetic resonance spectroscopy. The R39E/R43E protein is a mixture of unfolded and folded protein suggesting that the protein can adopt a wild type conformation but that the three dimensional structure is unstable. The A45I and V46E mutated proteins have the same structure and stability as the wild type protein. These results describe for the first time specific derivatives of p17 that can adopt the wild type structure, which are produced at normal levels in the infected cell but which are severely defective in terms of viral infectivity. Proteins of this type have a strong possibility of being able to interfere with the functions of the normal viral p17 protein. This is because they are present in significant amounts and they are in a wild type conformation that could be expected to allow normal interactions with other viral and cellular proteins. Indeed it is already known that certain mutated Gag proteins can be assembled together with normal proteins into viral particles (Lee and Linial 1995; Zhao et al 1994).

We have therefore discovered novel non-functional derivatives of p17 proteins that can be expressed at wild type levels in the cell. These data allow us to predict that these mutant proteins would, if co-expressed with normal viral proteins, have the opportunity to interfere with normal wild type protein function by competing for the key primary interactions that are critical for forming the basic structural trimeric unit.

2. A search for inhibitory peptides

A model for the assembly of HIV viral cores via the formation of assembly intermediates has been proposed. In the case of the matrix formed by p17 it is proposed that p17 monomers associate to form trimers which then pack together to form the shell like structure of the matrix (Nermut et al 1994; Hill et al 1996). Trimer formation must involve intimate interactions between tine exposed surfaces of the p17 monomers. It should therefore be possible to block these interaction by providing an analogous or homologous surface. Briefly the method used was as follows:

Peptide inhibition experiments

A series of overlapping p17 derived 1 5mer peptides were used. The peptides were dissolved in phosphate-buffered saline pH 7.0 and used at a final concentration of 200 mg/ml. For each peptide, $2\times10^5$ U937 cells were pelleted and resuspended in 500 ml media containing 50 ml of a stock of HIV-$1_{IIIB}$ virus (giving a multiplicity of infection of 0.25) and 200 mg/ml of the appropriate peptide. Following incubation for two days, the cells were pelleted and resuspended in fresh media containing peptide. After a further three days incubation, 100 ml of the culture was removed and added to $1\times10^5$ C8166 cells in a total volume of 500 ml with the appropriate peptide. Samples of both the U937 and C8166 culture supernatants were taken after a further two and three days incubation and assayed for RT activity. In addition, the C8166 cells were visually inspected for the appearance of syncytia on day three.

As shown in Table 2 we identified two inhibitory peptides spanning residues 31 to 45 (peptide 1) and 41 to 55 (peptide 2). The first peptide has not been previously identified and in fact previous studies using a larger peptide spanning 23 to 46 showed no inhibitory effect of this region (Neidrig et al 1994). The second peptide encompasses part of a previously identified peptide (Neidrig et al 1994) but significantly it contains residues 45 and 46 which our mutagenesis clearly defines as critical for infectivity. Peptides 31–45 and 41–55 have not therefore been previously described as inhibitors of HIV-1 replication.

TABLE 1

Properties of p17 mutants

| | | Particle Production | | | Infectivity | | |
|---|---|---|---|---|---|---|---|
| Mutant[a] | Side-chain[b] | RT[c] | Western | EM | C8166[d] | H9[e] | MAGI[f] |
| Wild-type | | +++ | normal | Mature, budding particles | +++ | +++ | 100 |
| Helix A | | | | | | | |
| R39E, R43E | exposed, charged | +++ | normal | re-location to cytoplasm | + | – | 0.3 |
| A–B loop | | | | | | | |
| F44H | exposed, hydrophobic | +++ | normal | Nd | +++ | +++ | nd |
| A451 | exposed, hydrophobic | +++ | normal | mature, budding particles | + | + | 7 |
| V4GE | exposed, hydrophobic | +++ | normal | mature, budding particles | + | ++ | 44 |
| N47D, ES5Q | exposed, charged | +++ | normal | | +++ | +++ | nd |
| L50A, L51A | Internal | + | low protein[1] | no particles | – | – | 0 |

TABLE 1-continued

Properties of p17 mutants

| Mutant[a] | Side-chain[b] | Particle Production | | | Infectivity | | |
|---|---|---|---|---|---|---|---|
| | | RT[c] | Western | EM | C8166[d] | H9[e] | MAGI[f] |
| Helix B | | | | | | | |
| C75S | internal | + | low protein | no particles | – | – | 0.2 |
| Q59E | exposed, charged | +++ | normal | nd | +++ | +++ | nd |
| Q63E | exposed, charged | +++ | normal | nd | +++ | +++ | nd |
| B–C loop | | | | | | | |
| T70A, S72A | exposed, hydrophilic | +++ | normal | nd | +++ | +++ | 60 |
| T70E, E7AK | exposed, hydrophilic | + | low protein | no particles | + | + | 0.9 |
| Helix C | | | | | | | |
| Y86R | internal | +++ | normal | nd | +++ | +++ | 70 |
| C87S | internal | +++ | normal | some normal particles | + | +++ | 5 |
| Y86R, C87S | internal | + | low protein | nd | – | – | nd |
| Helix D | | | | | | | |
| E107K, K110E | exposed, charged | +++ | normal | nd | +++ | +++ | nd |
| K(110–114)Q[g] | exposed, charged | +++ | normal[l] | nd | +++ | ++ | nd |
| K(110–114)E | exposed, charged | +++ | normal[l] | nd | +++ | +++ | nd |

[a]mutants named according to amino acid substitution
[b]position and characteristics of side chain of wild-type residue
[c]reverse transcriptase activity +++ wild-type + less than 20% wild-type
[d]syncytia scored 48 hours post-infection +++ wild type + few syncytia
[e]. . time to peak RT activity in H9 cells +++ wild-type ++ delayed by 2–5 days + delayed by more than 20 days
[f]no. blue cells per field of view relative to wild-type
[g]mutant is K110Q, K112Q, K113Q, K114Q
[h]reduced levels of viral proteins seen on Western
[l]normal profile but mobility of p17 altered
nd-not determined

TABLE 2

Inhibition of HIV-1 infectivity by p17-derived peptides

| | RT titer × 10³ cpm/ml[b] | | | | Syncytia[c] |
|---|---|---|---|---|---|
| | U937 | | | C8166 | |
| Peptide[a] | day 7 | day 8 | day 2 | day 3 | day 3 |
| None | 3.2 | 6.7 | 3.9 | 11.4 | + |
| 31–45 | – | – | – | – | |
| 41–55 | – | – | – | – | |
| 51–65 | 14.8 | 47.0 | 19.9 | 33.6 | + |
| 61–75 | 2.1 | 5.7 | 15.4 | 21.9 | + |
| 71–85 | – | 1.1 | 3.9 | 3.6 | + |

[a]corresponding p17 residues
[b]RT activity in supernatant at indicated timepoints following challenge with HIV-1
[c]syncytia in C8166 cells.

TABLE 3

| HIV-1 GAG | | SEQ ID NO: |
|---|---|---|
| CONSENSUS.A | START HELIX A ↓    PEPTIDE 2   45 46<br>                  39   43 ↓↓<br>mGARaSvLsgqklDdwekIrLRPgGkXkYrLXHlvwasreLerFaLnPslLeT?egcggimeQiq3alkT | 69–27 |
| HIVU455 | M---A-V-SCKK--SWEK-R---G-N-K-RL--LVW-SRE-EK-T-N-GL-E-AEGCQQILG-LQPALQ- | 70–34 |

TABLE 3-continued

| HIV-1 GAG | | SEQ ID NO: |
|---|---|---|
| HIVUG266 | M---V-V-SEGK--A EK-R---E-K-K-KL--LV -SRE-EK-A-N-SL-E-TEGCQRILE-LQPALQ- | 68-35 |
| HIVMAL | M---A-V-SGGK--AWEK-R---G-K-K-RL--LVW-SRE-ER-A-N-GL-E-GEGCQQIME-LQSTLK- | 70-36 |
| HIVVI32 | M---A-V-SGGK--AWEK-R---G-K-K-RM--LVW-SRE-DR-A-N-SL-E-KEGCQQIME-LESALK- | 70-37 |
| HIVVI57 | M---A-V-SGGK--AWEK-R---G-K-K-RL-LVW-SRE-ER-A-N-SL-E-TEGCQQILE-LQPALK- | 70-38 |
| HIVVI59 | I---A-V-SEGK--AXEK-R---G-K-Q-RL--LVX-SKE-ER-A-N-SL-E-TEGCQQIIE-LQPALK- | 70-39 |
| HIVVI310 | M---A-V-SGGK--KWEK-R---G-K-Q-RL--LVW-SRE-ER-A-N-SL-E-TEGCQQIIE-LQPALK- | 70-40 |
| HIVVI354 | M---A-I-SGGK--AWKR-R---G-K-K-QI--IVW-SRK-EK-A-N-GL-K-AEGCQQIME-LQSALK- | 70-41 |
| HIVVI415 | M---A-V-SGGK--AWEK-R---G-R-K-RM--LVW-SRE-DR-A-N-GL-E-AEGCQQILE-LQPALK- | 70-42 |
| HIVK7 | I---A-V-SGGQ--RXEK-R---G-K-K-RL--LVW-SRE-ER-A-N-SL-E-TERCQQIME-LQSALK- | 70-43 |
| HIVK29 | M---A-V-SGGK--AWEK-R---G-K-K-RM--LVW-SRE-ER-A-N-SL-E-TEGCQQIIE-LQPALK- | 70-44 |
| HIVK88 | M---A-V-SGGK--AWEK-R---GK-K-RM--LVW-SRE-DR-A-N-SL-E-AEGCQQIME-LQSALK- | 70-45 |
| HIVK89 | M---A-V-SGGK--TWEK-R---G-K-K-KL--LVW-SRE-ER-A-N-SL-E-TEGCQQIME-LQPALK- | 70-46 |
| HIVK98 | M---T-V-SGGK--AWEK-R---G-N-R-KL--IVW-SRE-ER-A-N-GL-E-TEGCQQIMK-LQSALQ- | 70-47 |
| HIVK112 | M---A-V-SGGK--AWEK-R---G-K-K-RI--LVW-SRE-EK-A-N-SL-E-TEGCQQIME-LQSALK- | 70-48 |
| HIVK124 | M---A-V-SGGK--AWEK-R---G-K-K-RL--LVW-SRE-ER-A-N-SL-E-TEGCQQIME-LQSSLK- | 70-49 |
| HIVCI4 | M---A-V-SGGK--AWEK-R---G-K-K-RM-LIW-GRE-ER-A-N-SL-E-TEGCQQIMA-LQSALK- | 70-50 |
| HIVCI20 | M000A0V0SGGK--AWEK-R---G-K-K-RL--LVW-SRE-ER-A-N-SL-E-AGGCQQLME-LQAHLR- | 70-51 |
| HIVCI32 | M---A-V-SGGR--AWEK-R---G-K-K-KL--LVW-SRE-ER-A-N-SL-E-SEGCQQLIE-FQSTLG- | 70-52 |
| HIVC151 | M---A-I-SGGK--SWEK-R---G-R-Q-RL--LVW-SRE-ER-A-N-SL-E-AEGCQQIIE-LQSALK- | 70-53 |
| HIVCI59 | M---A-V-SGGK--AWEK-R---G-K-K-RL--LVW-SRE-ER-A-N-GL-E-ADGCQQLME-LQSALR- | 70-54 |
| HIVG141 | M---A-V-SGGK--DWEK-Q---G-T-R-KL--IVW-SRE-ER-A-D-SL-E-SEGCKQILG-LQPALK- | 70-55 |
| HIVTN238 | M---A-V-TGGK--AWEK-R---G-R-K-KI--LVW-SRE-ER-A-N-GL-E-VEGCQQIIE-LQSTLK- | 70-56 |
| HIVTN243 | M---A-V-SGGK--AWEK-R---G-K-K-RM--LVW-SRE-ER-A-N-GL-E-AEGCQQIIE-LQSTLK- | 70-57 |
| HIVTN240 | M---A-V-SGGK--AWEK-R---G-R-K-RL--LVW-SRE-ER-A-N-SF-E-AEGCQQIIE-LQSTLK- | 70-58 |
| HIVTN245 | M---A-V-SGGK--AWEK-R---G-R-K-KM--LVW-SRE-ER-A-N-GL-E-AEGRQQIIR-LQSTLK- | 70-59 |
| HIVLBV105 | M---A-V-SGGK--TWEK-R---G-K-K-RM--LVW-SRE-ER-A-N-GL-E-AEGCQQILE-LQPSVK- | 70-60 |
| HIVLBV23 | M---A-V-SGGK--AWER-R---G-K-K--RM-LVW-SRE-ER-A-N-GL-E-AEGCQQIMG-LQTALQ- | 70-61 |
| HIVLBV2310 | M---A-V-SGGK--SWEK--SWEK-R---G-K-K-RL--LVW-SRE-ER-A-N-GL-E-AEGCQQLME-LQSALR- | 70-62 |
| HIVIC144 | M---A-V-SGGK--AWEK-R---G-K-K-RL--LVW-SRE-ER-A-N-GF-E-AEGCQQLME-LQSTLK- | 70-63 |
| HIVDJ258 | M---A-V-SGGK--SWEK-R---G-K-K-RL--LWV-SRE-ER-A-N-GL-E-AEGCQQLME-LQSALG- | 70-64 |
| CONSENSUS.B | MGARASVLSgGeLDrWekIRLRPgGKKkYkLKHiVWASReLERFAvnPgLLEtseGCRqIlgQLqPsLaT | 70-28 |
| HIVSF2 | ---------G-E--K-EK-----G---K-K---I-----E-----VN-G---TSE---Q-LG--Q-S-Q- | 70-65 |
| HIVBZ167 | ---------G-E--R-EK-----G---K-R---V-----E-----VN-G---TAA---Q-LG--Q-S-Q- | 70-66 |
| HIVBZ190 | ---------G-K--R-EK-----G---R-Q---I-----E-----VN-G---TAE---Q-LG--Q-S-Q- | 70-67 |
| HIVBZ200 | ---------G-E--K-EK-----G---A-K---I-----E-----VN-G---TSE---K-IG--Q-S-Q- | 70-68 |
| HIVPH136 | ---------G-E--R-ER-----G---K-K---I-----E-----VN-G---TSG---Q-LE--Q-A-Q- | 70-69 |
| HIVPH153 | ---------G-K--R-EK-----G---K-Q---I-----E-----VN-G---TSE---Q-LG--H-A-Q- | 70-70 |
| HIVTB132 | ---------G-Q--R-KK-----G---K-R---I-----E-----VN-G---TSE---Q-LG--Q-S-Q- | 70-71 |

TABLE 3-continued

| HIV-1 GAG | | SEQ ID NO: |
|---|---|---|
| HIVLAI | ---------G-E--R-EK-----G---K-K---I-----E-----VN-G---TSE---Q-LG--Q-S-Q- | 70-28 |
| HIVHXB2R | ---------G-E--R-EK-----G---K-K---I-----E-----VN-G---TSE---Q-LG--Q-S-Q- | 70-28 |
| HIVBH102 | ---------G-E--R-EK-----G---K-K---I-----E-----VN-G---TSE---Q-LG--Q-S-Q- | 70-28 |
| HIVPV22 | ---------G-E--R-EK-----G---K-K---I-----E-----VN-G---TSE---Q-LG--Q-S-Q- | 70-72 |
| HIVMN | ---------G-E--R-EN-----G---K-K---V-----E-----VN-G---TSE---Q-LG--Q-S-Q- | 70-28 |
| HIVJH3 | ---------G-E--R-EK-----G---K-K---I-----E-----VN-S---TSE---Q-LG--Q-S-Q- | 70-73 |
| HIVJRCSF | ---------G-E--R-EK-----G---K-R---I-----E-----VN-G---SSE---Q-LG--Q-S-K- | 70-74 |
| HIVOYI | ---------G-E--K-EK-----G---K-Q---I-----E-----IN-G---TSE---Q-LG--Q-S-K- | 70-75 |
| HIVNY5CG | ---------G-E--K-EK-----G---Q-R---I-----E-----VN-G---TSE---Q-LR--Q-S-Q- | 70-76 |
| HIVNL43 | ---------G-E--K-EK-----G---Q-K---I-----E-----VN-G---TSE---Q-LG--Q-S-Q- | 70-77 |
| HIVCDC4 | ---------G-E--R-EK-----G---Q-R---I-----K-----VN-G---TSK---Q-LG--Q-S-Q- | 70-78 |
| HIVHAN | ---------G-E--K-EK-----G---K-Q---I-----E-----VN-G---TSE---Q-MG--Q-S-Q- | 70-65 |
| HIVCAM1 | ---------G-E--K-EK-----G---K-K---I-----E-----VN-G---TSE---Q-LG--Q-S-Q- | 70-79 |
| HIVRF | ---------G-K--K-EK-----R---R-K---I-----E-----VN-S---TAE---Q-LG--Q-A-Q- | 70-80 |
| HIVD31 | ---------G-E--R-EK-----G---K-R---I-----E-----VN-G---TSE---Q-LG--Q-S-Q- | 70-81 |
| HIVJRFL | ---------G-K--K-EK-----G---K-R---I-----E-----VN-G---SSE---Q-LG--L-S-K- | 70-82 |
| HIVUG280 | ---------G-E--R-EK-----G---K-K---I-----E-----VN-G---TSE---Q-LG--Q-A-Q- | 70-83 |
| HIVYU2 | ---------A-E--K-EK-----G---Q-R---I-----E-----VD-G---TSE---Q-LG--Q-S-Q- | 70-83 |
| CONCSEN-SUS.C | MGARASiLrGgKLD?WEkIrLrPGGkKhYMiKHLVWASRELerFALnpgLLETseGCkqLqPalQT | 69-29 |
| HIVUG268 | ------V-R-G---T--K-K-R---K-C--M----------GR---NSG----SE--KQ-MKQ-Q-AL-- | 70-84 |
| HIVSM145 | ------I-R-G---A--R-R-R---K-H--I----------ER---NPG----SE--KQ-MKQ-Q-AL-- | 70-85 |
| HIVZAM18 | ------I-K-G---T--R-K-R---K-H--I----------ER---NPG----SE--KQ-IKQ-Q-SI-- | 70-86 |
| HIVZAM19 | ------I-X-G---A--R-R-R---K-H--I----------ER---NPG----SE--KQ-IKQ-Q-AL-- | 70-87 |
| HIVZAM20 | ------I-R-G---K--R-R-R---K-H--I----------ER---NPG----AD--KQ-IRQ-H-AL-- | 70-88 |
| HIVDJ259 | ------I-R-E---A--K-K-R---R-R--L----------EK---NPS----SE--KQ-IRQ-Q-AL-- | 70-89 |
| HIVVI313 | ------I-R-G---T--R-K-K---K-H--M----------ER---DPG----SQ--RE-IXX-Q-AL-- | 70-90 |

|———PEPTIDE 1———|

| CONSENSUS.D | |———PEPTIDE 1———| | 68-30 |
| | MGARASVLsGGkLD?WEkIrLRPGgkXXY7LXYivWASRELeRid1NPGLLETseCCkQIigQLqPsigt | |
| HIVELI | ---------S--K--K--K-R----GK---R-----IV------E-YAL-------SE-K--IG--Q-AIQT | 70-91 |
| HIVNDK | ---------S--K--T--R-R----GK---A----LI------E-FTL-------SE-K--IG--Q-SIQT | 70-92 |
| HIVZ2Z6 | ---------S--K--A--K-R----GK---R----LV------E-FAL-------SD-K--IG--Q-AIRT | 70-93 |
| HIVVI203 | ---------T--K--S--K-R----GK---R-----IV------E-FAL-------SE-K--IE--Q-SIQT | 70-94 |
| HIVVI205 | ---------S--K--Q--K-R----KS---R-----IV------K-FAL-------SE-R--IE--Q-AIQT | 70-95 |
| HIVG109 | ---------S--Q--A--R-R----GK---Q-----IV------E-FAL-------AE-K--IE--H-NLQS | 70-96 |
| HIVK31 | ---------S--K--E--K-Q----GH---K-----IV------E-FAI-------PE-K--MG--H-AIQT | 70-97 |
| HIVUG274 | ---------S--K--E--K-R----GN---K-----IV------E-FAI-------SE-K--MG--Q-ALXT | 70-98 |
| HIVUG270 | ---------S--K--E--K-R----GN---K-----LV------E-FAL-------SE-K--MG--Q-SIQT | 70-99 |

TABLE 3-continued

| HIV-1 GAG | | SEQ ID NO: |
|---|---|---|
| HIVSE365 | ---------S--Q--R--K-R----GK---K---IV------E-FAL-------SE-R--IG--Q-AIQT | 70-100 |
| CONSENSUS (E) | MGARASVLSGGKLDAWEKIrLRPGGkKKYrmKHLvWASRELERFAidPGLLETsEGCrKIIGQLQpSLQT | 70-31 |
| HIVVI174 | -------------------Q-----K---RM---V----------ID------P---R-------T---- | 70-101 |
| HIVVI69 | -------------------R-----R---KM---I----------LD------S---R-------P---- | 70-102 |
| HIVBZ162 | -------------------R-----K---RL---V----------IN------S---Q-------P---- | 70-103 |
| CONSENSUS.O | MGArASVLsGgkLDaWEkiRLrPGgkKkYrlKHLVWAsrELerfAlnpgLlet?EGc?q???QLqPalkt | 6532 |
| HIVVI191(F) | ---R----S-GK--A--KI--R--GK-Q-RI------SR--EKF-LNPG-LETT--CQQIMR--Q-ALQT | 70-104 |
| HIVLBV217 (F) | ---R----S-GK--E--KI--R--GK-K-RM------SR--ERF-LNPG-LETT--CQQILQ--Q-SLQT | 70-105 |
| HIVVI515(G) | ---R----S-GR--A--KI--R--GK-Q-RL------SR--ERF-LNPG-LETS--CLQIIE--Q-ALKT | 70-106 |
| HIVVI557(G) | ---R----S-GK--A--KI--R--GK-K-RL------SR--ERF-LNPD-LDTA--CLQLIE--Q-ALKT | 70-107 |
| HIVVI325 | ---R----S-GK--T--KI--R--GS-K-RL------SR--ERF-LNPS-LETT--CRQIIR--Q-SLQT | 70-108 |
| HIVANT70 | ---S----T-SK--A--QI--K--SK-K-RL------SR--ERF-CNPE-LETA--NEKLLQ--E-ALKT | 70-109 |
| HIVMVP51 | ---R----T-SK--A--RI--R--SK-A-RL------SR--ERY-CNPG-LETA--TEQLLQ--E-ALKT | 70-110 |
| CPZGA3 | ---R----T-GX--R--KV--R--GR-R-MM------SR--ERF-CDPG-MESX--CTKLLQ--E-ALXT | 70-111 |

|—PEPTIDE 2—|

TABLE 4

| | | SEQ ID NO: |
|---|---|---|
| CONSENSUS | | 69-33 |

```
            PEPTIDE 1           39    45  46
MCarnSVLsGXkaDELEkiRLRPcGXXkYmLXH?vWAaNeLDrFGLaESLLesKEGCqkIlsVLaPlVPT
```

| HIV2ROD | --ARN---R--KA----RI----G---K-R---IV--A-K--R---A----ES----QK-LT--D-M--- | 70-112 |
|---|---|---|
| HIV2NIHZ | --ARN---R--KA----KI----G---K-K---IV--A-E--R---A----ES----QK-LT--D-L--- | 70-113 |
| HIV2ISY | --AKN---R--KA----KI----G---K-R---IV--A-E--R---T----ES----QK-IS--E-L--- | 70-114 |
| HIV2ST | --ARN---R--KA----KI----G---K-K---IV--A-E--R---A----ES----QK-LT--D-L--- | 70-115 |
| HIV2B3N | --ARN---R--KA----KV----G---K-R---IV--A-E--K---A----ES----QK-LR--D-L--- | 70-116 |
| HIV2CAM2 | --ARN---R--KA----KV----G---K-K---IV--A-E--R---A----ES----QR-LK--D-L--- | 70-117 |
| HIV2D194 | --ARN---R--KA----KV----N---R-R---VV--A-E--R---A----ES----QK-LK--E-L--- | 70-118 |
| HIV2GH1 | --ARN---R--KA----KI----S---K-R---IV--A-E--K---A----ES----QK-LT--D-L--- | 70-119 |
| HIV2D205 | --ARG---S--KT----KV----G---K-M---VV--V-E--R---A----ES----QK-LK--A-L--- | 70-120 |
| HIV2UC1 | --ARS---S--KT----KV----G---R-C---II--V-E--R---A----ES----HK-LT--A-L--- | 70-121 |
| SIVMM251 | --ARN---S--KA----KI----G---K-M---VV--A-E--R---A----EN----QK-LS--A-L--- | 70-122 |
| SIVMM32H | --ARN---S--KA----KI----G---K-M---VV--A-E--R---A----EN----QK-LS--A-L--- | 70-123 |
| SIVMM1A11 | --ARN---S--KA----KI----N---K-M---VV--A-E--R---A----EN----QK-LS--A-L--- | 70-124 |
| SIVMM142 | --ARN---S--KA----KI----G---K-M---VV--A-E--R---A----EN----QK-LS--A-L--- | 70-125 |
| SIVMM239 | --VRN---S--KA----KI----N---K-M---VV--A-E--R---A----EN----QK-LS--A-L--- | 70-126 |
| SIVMNE | --ARN---S--KA----KI----G---K-M---VV--A-E--R---A----EN----QK-LS--A-L--- | 70-127 |
| SIVSMMH4 | --ARN---S--EA----KV----N---K-M---VV--A-E--R---A----DN----QK-LS--A-L--- | 70-128 |

TABLE 4-continued

|  |  | SEQ ID NO: |
|---|---|---|
| SIVSMMH9 | --VRN---S--KA----KI----G---K-M---IV--A-E--R---A----EN----QK-LS--A-L--- | 70-129 |
| SIVSMMPBJ | --ARN---S--KA----KI----G---R-Q---IV--A-E--R---A----EN----QK-LS--A-L--- | 70-130 |
| STVSTM | --ARS---S--KA----KV----G---K-M---VV--A-E--R---A----ES----QK-IT--E-L--- | 70-131 |

PEPTIDE 2

| CONSENSUS | GSENLKSL?NEveViwCiHAEEKvK?TEeAKqivqRHLvaeTgtaekMP?tsrPTAPpSqrggNyPVQg?    p16\ /p28 | 135-33 |
| HIV2ROD | --------F-TVC-IW-I-----V-D--G--QIVR---VAE-GTAEK--STSR----S-EKGG-Y---H. | 139-112 |
| HIV2NIHZ | --------F-TVC-IW-I-----V-D--G--QIVQ---VAE-GTAEK--NTSR----P-GK...-Y---Q. | 137-113 |
| HIV2ISY | --------Y-TTC-IW-L-----V-D--E--RIVG---VAE-ETAEK--NISR----P-GKGG-F---Q. | 139-114 |
| HIV2ST | --------F-TVC-IW-I-----A-D--E--QKVQ---VAE-KTTEK--STSR----P-GNGG-F---Q. | 139-115 |
| HIV2BEN | --------F-TVC-IW-L-----V-D--E--KLAQ---VAE-GTAEK--NTSR----P-GKRG-Y---Q. | 139-116 |
| HIV2CAM2 | --------F-TVC-IW-I-----V-D--E--RIAL---AAE-GTAEK--DTSR----P-GKGG-Y---S. | 139-117 |
| HIV2D194 | --------F-TVC-IW-L-----V-D--E--KLAQ---VAE-GTAEK--NISR----P-GKGG-F---Q. | 139-118 |
| HIV2GH1 | --------F-TVC-IW-L-----V-D--E--KLVQ---GAE-GTAEK--STSR----P-GRGR-F---QT | 140-119 |
| HIV2D205 | --------F-IVC-IF-l-----V-D--E--KIAQ---AAD-...EK--ATNK----P-G..G-Y---Q. | 134-120 |
| HIV2UC1 | --------F-TVC-IY-L-----V-D--E--KIAQ---AAD-...EK--ATSR----P-G..G-Y---Q. | 134-121 |
| SIVMM251 | --------Y-TVC-IW-I-----V-H--E--QIVQ---VVE-GTAET--KTSR----S-GRGG-Y---Q. | 139-122 |
| SIVMM32H | --------Y-TVC-IW-I-----V-H--E--QIVQ---VVE-GTAET--KTSR----S-GRGG-Y---Q. | 139-123 |
| SIVMM1A11 | --------Y-TVC-IW-I-----V-H--E--QIVQ---VVE-GTAEI--KTSR----S-GRGG-Y---Q. | 139-124 |
| SIVMM142 | --------Y-TVC-IW-I-----V-H--E--QIVQ---VME-GTAET--KTSR----F-GRGG-Y---Q. | 139-125 |
| SIVMM239 | --------Y-TVC-IW-I-----V-H--E--QIVQ---VVE-GTTET--KTSR----S-GRGG-Y---Q. | 139-126 |
| SIVMNE | --------Y-TVC-IW-I-----V-H--E--QIVQ---VVE-GTAET--KTSR----S-GRGG-Y---Q. | 139-127 |
| SIVSMMH4 | --------Y-TVC-IW-I-----V-H--E--QIVQ---VVE-GTADR--ATSR----P-GRGG-Y---Q. | 139-128 |
| SIVSMMH9 | --------Y-TVR-LW-I-----V-H--E--QIVQ---VVE-GTADK--ATSR----P-GRGG-Y---Q. | 139-129 |
| SIVSMMPBJ | --------F-TVC-LW-I-----V-H--E--QIVQ---VVE-GTADK--ATSR----P-GKGG-Y---Q. | 139-130 |
| SIVSTM | --------F-TVC-IW-I-----V-H--E--QVVK---VVE-GTANK--ATSR----P-GRGG-Y---Q. | 139-131 |

TABLE 5

Database Accession Nos. for Tables 3 and 4
HIV1GAG.sl-tbl at hiv-web.lanl.gov

| COMMON NAME | LOCUS | ACC # | FIRST AUTHORS | REFERENCE |
|---|---|---|---|---|
| SUBTYPE A: | | | | |
| U455 | HIVU455 | M62320 | Oram, J. D. | ARHR 6, 1073 (1990) |
| BZ126B | HIVBZ126B | L22083 | Louwagie, J. J. | ARHR 10, 561 (1994) |
| IBNG | HIVIBNG | L39106 | Howard, R. M. | ARHR 10, 1755 (1994) |
| VI59 | HIVVI59 | L11795 | Louwagie, J. J. | AIDS 7, 769 (1993) |
| VI310 | HIVVI310 | L11786 | Louwagie, J. J. | AIDS 7, 769 (1993) |
| VI57 | HIVVI57 | L11794 | Louwagie, J. J. | AIDS 7, 769 (1993) |
| K112 | HIVK112 | L11768 | Louwagie, J. J. | AIDS 7, 769 (1993) |
| K88 | HIVK88 | L11773 | Louwagie, J. J. | AIDS 7, 769 (1993) |
| K29 | HIVK29 | L11770 | Louwagie, J. J. | AIDS 7, 769 (1993) |
| K7 | HIVK7 | L11772 | Louwagie, J. J. | AIDS 7, 769 (1993) |
| K98 | HIVK98 | L11775 | Louwagie, J. J. | AIDS 7, 769 (1993) |
| K89 | HIVK89 | L11774 | Louwagie, J. J. | AIDS 7, 769 (1993) |
| VI32 | HIVVI32 | L11788 | Louwagie, J. J. | AIDS 7, 769 (1993) |

TABLE 5-continued

Database Accession Nos. for Tables 3 and 4
HIV1GAG.sl-tbl at hiv-web.lanl.gov

| COMMON NAME | LOCUS | ACC # | FIRST AUTHORS | REFERENCE |
|---|---|---|---|---|
| VI415 | HIVVI415 | L11791 | Louwagie, J. J. | AIDS 7, 769 (1993) |
| CI4 | HIVCI4 | L11757 | Louwagie, J. J. | AIDS 7, 769 (1993) |
| LBV23 | HIVLBV23 | L11777 | Louwagie, J. J. | AIDS 7, 769 (1993) |
| TN2431 | HIVTN2431 | L03702 | McCutchan, F. E. | ARHR 8, 1887 (1992) |
| TN245 | HIVTN245 | L11762 | Louwagie, J. J. | AIDS 7, 769 (1993) |
| TN240 | HIVTN240 | L11761 | Louwagie, J. J. | AIDS 7, 769 (1993) |
| CI20 | HIVCI20 | L11755 | Louwagie, J. J. | AIDS 7, 769 (1993) |
| CI59 | HIVCI59 | L11759 | Louwagie, J. J. | AIDS 7, 769 (1993) |
| LBV2310 | HIVLBV2310 | L11779 | Louwagie, J. J. | AIDS 7, 769 (1993) |
| CI51 | HIVCI51 | L11758 | Louwagie, J. J. | AIDS 7, 769 (1993) |
| IC144 | HIVIC144 | L11767 | Louwagie, J. J. | AIDS 7, 769 (1993) |
| DJ258 | HIVDJ258 | L11763 | Louwagie, J. J. | AIDS 7, 769 (1993) |
| TN238 | HIVTN238 | L11760 | Louwagie, J. J. | AIDS 7, 769 (1993) |
| UG266 | HIVUG266 | L11798 | Louwagie, J. J. | AIDS 7, 769 (1993) |
| SUBTYPE B: | | | | |
| SF2 | HIVSF2 | K02007 | Sanchez-Pescador, R. | Science 227, 484 (19: |
| BZ167 | HIVBZ167 | L11752 | Louwagie, J. J. | AIDS 7, 769 (1993) |
| PH153 | HIVPH153 | L11781 | Louwagie, J. J. | AIDS 7, 769 (1993) |
| PH136 | HIVPH136 | L11780 | Louwagie, J. J. | AIDS 7, 769 (1993) |
| TB132 | HIVTB132 | L03697 | McCutchan, F. E. | ARHR B, 1887 (1992) |
| BZ190 | HIVBZI90 | L11753 | Louwagie, J. J. | AIDS 7, 769 (1993) |
| LAI | HIVLAI | K02013 | Wain-Hobson, S. | Cell 40, 9 (1985) |
| HXB2R | HIVHXB2R | K03455 | Starcich, B. | Science 227, 538 (19: |
| MN | HIVMN | M17449 | Gurgo, C. | Virol. 164, 531 (198: |
| JH31 | HIVJH31 | M21137 | Koniyama, N. | ARHR 5, 411 (1969) |
| JRCSF | HIVJRCSF | M38429 | Koyanagi, S. | Nature 348, 69 (1990; |
| JRFL | HIVJRFL | M74978 | O'Brien, W. A. | Nature 348, 69 (1990: |
| OYI | HIVOYI | M26727 | Wain-Hobson, S. | AIDS 3: 707 (1989) |
| NY5CG | HIVNY5CG | M38431 | Theodore, T. | PNASU 83: 5038 (1986: |
| NL43 | HIVNL43 | M19921 | Buckler, C. E. | JVI 59: 284 (1986) |
| CDC41 | HIVCDC41 | M13136 | Desai, S. M. | PNAS 83, 8380 (1986) |
| HAN | HIVHAN | U43141 | Sauemann, U. | ARHR 6, 813 (1990) |
| CAM1 | HIVCAM1 | D10112 | McIntosh, A. | Unpublished (1991) |
| RF | HIVRF | M17451 | Starcich, B. R. | Cell 45, 637 (1986) |
| D31 | HIVD31 | U43096 | Dietrich, U. | Unpublished (1992) |
| UG280 | HIVUG280 | L11802 | Louwagie, J. J. | AIDS 7, 769 (1993) |
| YU2 | HIVYU2 | M93258 | Li, Y. | JVI 65, 3973 (1991) |
| BCSG3C | HIVBCSG3C | L02317 | Ghosh, S. K. | Virol. 194, 658 (199 |
| P896 | HIVP896 | M96155 | Collman, R. | JVI 66, 7517 (1992) |
| 3202A12 | HIV3202A12 | U34603 | Guillon, C. | ARHR 11, 1537 (1995) |
| 3202A21 | HIV3202A21 | U34604 | Guillon, C. | ARHR 11, 1537 (1995) |
| GAG46 | HIVGAG46 | U29413 | Yoshimur, F. K. | Unpublished (1995) |
| MANC | HIVMANC | U23487 | Zhu, T. | Nature 3745, 503 (19 |
| GAG314 | HIVGAG314 | U29404 | Yoshimura, F. K. | Unpublished (1995) |
| GAG22 | MTVGAG22 | U29255 | Yoshimura, F. K. | Unpublished (1995) |
| GAG15 | HIVGAG15 | U29246 | Yoshimura, F. K. | Unpublished (1995) |
| WEAU160 | HIVWEAU160 | U21135 | Ghosh, S. | Unpublished (1995; |
| SUBTYPE C: | | | | |
| UG268 | HIVUG268 | L11799 | Louwagie, J. J. | AIDS 7, 769 (1993) |
| SM145 | HIVSM145 | L11803 | Louwagie, J. J. | AIDS 7, 769 (1993) |
| ZAM18 | HIVZAM18 | L03705 | McCutchan, F. | JAIDS 5, 441 (1992) |
| ZAM19 | HIVZAM19 | L03706 | McCutchan, F. E. | JAIDS 5, 441 (1992) |
| ZAM20 | HIVZAM20 | L03707 | McCutchan, F. | JAIDS 5, 441 (1992) |
| DJ259 | HIVDJ259 | L11764 | Louwagie, J. J. | AIDS 7, 769 (1993) |
| VI313 | HIVVI313 | L11787 | Louwagie, J. J. | AIDS 7, 769 (1993) |
| SUBTYPE D: | | | | |
| ELI | HIVELI | K03454 | Alizon, M. | Cell 46, 63 (1986) |
| Z2Z6 | HIVZ2Z6 | M22639 | Theodore, T. | Unpublished (1988) |
| NDK | HIVNDK | M27323 | Spire, B. | Gene 81, 275 (1989) |
| VI205 | HIVVI205 | L11785 | Louwagie, J. J. | AIDS 7, 769 (1993) |
| G109 | HIVG109 | L11765 | Louwagie, J. J. | AIDS 7, 769 (1993) |
| K31 | HIVK31 | L11771 | Louwagie, J. J. | AIDS 7, 769 (1993) |
| UG274 | HIVUG274 | L11801 | Louwagie, J. J. | AIDS 7, 769 (1993) |
| UG270 | HIVUG270 | L11800 | Louwagie, J. J. | AIDS 7, 769 (1993) |
| SE365 | HIVSE365 | L11797 | Louwagie, J. J. | AIDS 7, 769 (1993) |
| VI203 | HIVVI203 | L11784 | Louwagie, J. J. | AIDS 7, 769 (1993) |
| SUBTYPE F: | | | | |
| VI174 | HIVVI174 | L11782 | Louwagie, J. J. | AIDS 7, 769 (1993) |
| VI69 | HIWI69 | L11796 | Louwagie, J. J. | AIDS 7, 769 (1993) |

TABLE 5-continued

Database Accession Nos. for Tables 3 and 4
HIV1GAG.sl-tbl at hiv-web.lanl.gov

| COMMON NAME | LOCUS | ACC # | FIRST AUTHORS | REFERENCE |
|---|---|---|---|---|
| BZ162 | HIVBZ162 | L11751 | Louwagie, J. J. | AIDS 7, 769 (1993) |
| VI325 | HIVVI325 | L11789 | Louwagie, J. J. | AIDS 7, 769 (1993) |
| BZ163B | HIVBZ163B | L22086 | Louwagie, J. J. | ARHR 10, 561 (1994) |
| SUBTYPE G: | | | | |
| LBV217 | HIVLBV217 | L11778 | Louwagie, J. J. | AIDS 7, 769 (1993) |
| VI191 | HIVVI191 | L11783 | Louwagie, J. J. | AIDS 7, 769 (1993) |
| JV831 | HIVJV831 | U13212 | Abimiku, A. G. | ARHR 10, 1581 (1994) |
| SUBTYPE H: | | | | |
| VI525 | HIWI525 | L11792 | Louwagie, J. J. | AIDS 7, 769 (1993) |
| VI557 | HIVVI557 | U09666 | Janssens, W. | ARHR 10, 877 (1994) |
| HYBRIDS: | | | | |
| AD_K124 | HIVK124 | L11769 | Louwagie, J. J. | AIDS 7, 769 (1993) |
| AD_MAL | HIVMAL | K03456 | Alizon, M. | Cell 46, 63 (1986) |
| AD_CI32 | HIVCI32 | L11756 | Louwagie, J. J. | AIDS 7, 769 (1993) |
| AD_G141 | HIVG141 | L11766 | Louwagie, J. J. | AIDS 7, 769 (1993) |
| AG_VI35 | HIVVI354 | L11790 | Louwagie, J. J. | AIDS 7, 769 (1993) |
| AG_LBV1 | HIVLBV105 | L11776 | Louwagie, J. J. | AIDS 7, 769 (1993) |
| BF_BZ20 | HIVBZ200 | L11754 | Louwagie, J. J. | AIDS 7, 769 (1993) |
| SUBTYPE O: | | | | |
| ANT70C | HIVANT70C | L20587 | Vanden Haesevelde, M. | JVI 68, 1586 (1994) |
| MVP5180 | HIVMVP5180 | L20571 | Gurtler, L. G. | JVI 66, 1581 (1994) |
| CPZ: | | | | |
| CPZGAB | SIVCPZGAB | X52154 | Huet, T. | Nature 345, 356 (199 |
| CPZANT | STVCPZANT | U42720 | Vanden Haesevelde, M. | Virol. In Press (19 |

EXAMPLES

Example 1

The production of the inhibitory peptides and proteins in vivo a) Expression of single peptides Nucleic acid sequences corresponding to peptides 1 and 2 are synthesised as oligonucleotides. An operational sequence for peptide 1 encompasses the sequence shown in bold in FIG. 1 from nucleotide 91 to 132 plus additional sequences at the 5' and 3' ends to ensure translation initiation and termination. An operational sequence for peptide 2 encompasses the sequence underlined in FIG. 2 from nucleotide 121 to 142 plus additional sequences at the 5' and 3' ends to ensure translation initiation and termination. Operational sequences are shown below with the peptide-encoding sequence in bold and flanking sequences for the correct expression of the peptide shown in plain type:

PEPTIDE 1 (PEP1)
ATGTTAAAACATATAGTATGGGCAAGCAGGGAG CTAGAACGATTCTGATAA [SEQ ID NO: 3]

PEPTIDE 2 (PEP2)
ATGCTAGAACGATTCGCAGTTAATCCTGGCCTGT TAGAAACATCATGATAA [SEQ ID NO: 4]

Various additional linker sequences are added to the operational peptide sequences to create oligonucleotides with desirable restriction endonuclease recognition sites for insertion of the operational sequences into vectors such as retroviral vectors. Sample oligonucleotides for insertion into vectors are shown below:

1. BamHI-EcoRI-PEP1-BglII-EcoRI
5'CCGGATCCGGAATTCGTCGACCATGTTAAAAC ATATAGTATGGGCAAGCAGGGAGCTAGAACGA TTCTGATAAAGATCTGGAATTCCGG-3' [SEQ ID NO: 5]

2. EcoRI-BglII-PEP2-BamHI-EcoRI
5'CCGGGAATTCAGATCTGTCGACCATGCTAGAA CGATTCGCAGTTAATCCTGGCCTGTTAGAAAC ATCATGATAAGGATCCGGAATTCCGG-3' [SEQ ID NO: 6]

Figure 3:
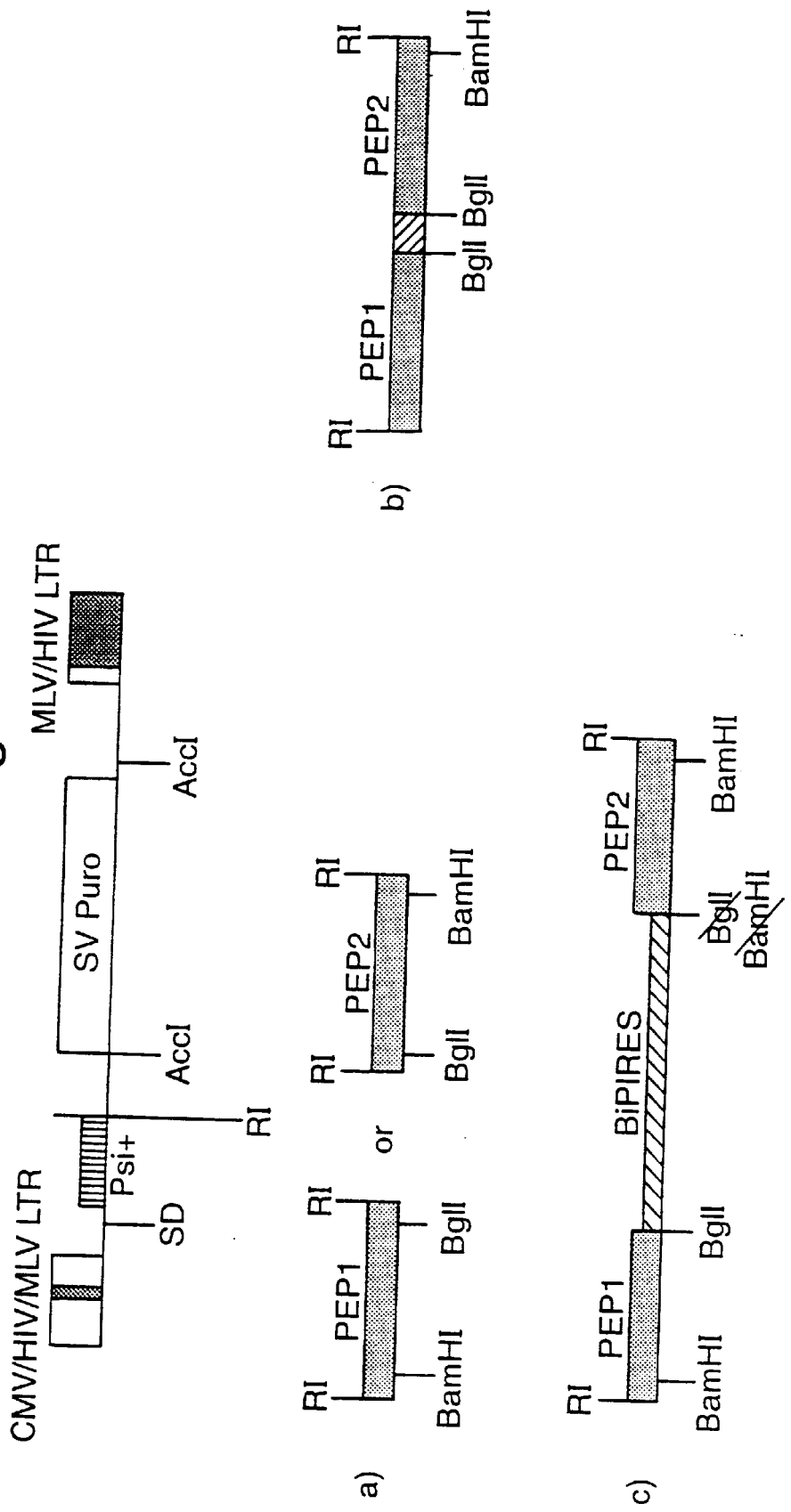
FIG. 3 shows a suitable system for expressing p17 or p16 peptides described herein, in a retroviral vector.

Sequences 1 and 2 above are cleaved with EcoRI and in this example the resulting fragments are inserted into the unique EcoRI site of pTIN500 (Cannon et al 1996). This produces retroviral vectors that express either peptide 1 or peptide 2 (FIG. 3(a)).

b) Expression of peptide polymers

Expression of the peptides as polymers is achieved by fusing the coding sequences described in section (a) above. The coding sequences are fused in such a way as to place a flexible linker between the two peptide coding sequences. A suitable linker may comprise amino acid repeats such as glycine-serine repeats. The purpose of the linker is to allow the correct formation and/or functioning of the independent peptides. It must be sufficiently long to achieve that purpose. The coding sequence of the flexible linker may be chosen such that it encourages translational pausing and therefore independent folding of protein products.

A person skilled in the art will be able to design suitable linkers. Some specific examples of suitable linkers are given below:

1. (Gly-Gly-Gly-Gly-Ser)$_3$ (SEQ ID NO: 21) as described in Somia et al., 1993 PNAS 90, 7889.

2. (Asn-Phe-lle-Arg-Gly-Arg-Glu-Asp-Leu-Leu-Glu-Lys-lle-lle-Arg-Gln-Lys-Gly-Ser-Ser-Asn) (SEQ ID NO: 22) from HSF-1 of yeast, see Wiederrecht et al., 1988 Cell 54, 841.

3. (Asn-Leu-Ser-Ser-Asp-Ser-Ser-Leu-Ser-Ser-Pro-Ser-Ala-Leu-Asn-Ser-Pro-Gly-lie-Glu-Gly-Leu-Ser) (SEQ ID NO: 23)from POU-specific OCT-1, see Dekker et al., 1993 Nature 362, 852 and Sturm et al., 1988 Genes and Dev. 2, 1582.

5. (Gln-Gly-Ala-Thr-Phe-Ala-Leu-Arg-Gly-Asp-Asn-Pro-Gln-Gly) from (SEQ ID NO: 24) RGD-containing Laminin peptide, see Aumailly et al., 1990 FEBS Lett.262, 82.

6. (Ser-Gly-Gly-Gly-Glu-lle-Leu-Asp-Val-Pro-Ser-Thr-Gly-Gly-Ser-Ser-Pro-Gly) (SEQ ID NO: 25) from LDV-containing linker, see Wickham et al., Gene Therapy 1995 2, 750.

In the present example PEP1 is fused to PEP2 via a flexible linker comprising three repeats of the sequence Gly-Gly-Gly-Gly-Ser (SEQ ID NO: 26).

The construction comprising Pep1-flexible linker-Pep2 is made with four separate oligonucleotide sequences. The final construction (SEQ ID NO: 7) and the four oligonucleotides (SEQ ID NOS: 8 to 11) are shown below:

SEQ ID NO: 7. A fusion gene for the expression of a Pep1/Pep2 fusion protein

5'CCGGATCCGGAATTCGTCGACC ATG TTA AAA CAT ATA GTA TGG GCA AGC AGG GAG CTA GAA CGA TTC AGA TCT ggt gga ggc ggt tca ggc gga ggt ggc tcg gga ggt gga gga tcg CTA GAA CGA TTC GCA GTT AAT CCT GGC CTG TTA GAA ACA TCA tga taa GAATTCCGGC -3' [SEQ ID NO:7]

PEP1 and PEP2 are in bold type; the flexible linker is in lower case; linker sequences containing sites for restriction enzymes are in upper case.

The DNA sequence (SEQ ID NO:7) is prepared as four oligonucleotides:

Oligonucleotide 1

5'CCGGATCCGGAATTCGTCGACC ATG TTA AAA CAT ATA GTA TGG GCA AGC AGG GAG CTA GAA CGA TTC AGA TC - 3' [SEQ ID NO:8]

Oligonucleotide 2

5'T ggt gga ggc ggt tca ggc gga ggt ggc tcg gga ggt gga gga tcg CTA GAA CGA TTC GCA GTT AAT CCT GGC CTG TTA GAA ACA TCA tga taa GAATTC-CGGC -3' [SEQ ID NO: 9]

Oliqonucleotide 3

5'T GAA TCG TTC TAG CTC CCT GCT TGC CCA TAC TAT ATG TTT TAA CAT GGTCGACGAATTTCCG-GATCCGG - 3' [SEQ ID NO: 10]

Oligonucleotide 4

5'GCCGGAATTC TIA ACA TGA TGT TTC TAA CAG GCC AGG ATT AAC TGC GAA TCG TTC tag cga tcc tcc acc tcc cga gcc acc tcc gcc tga acc gcc tcc acc AGA TC -3' [SEQ ID NO: 11]

Oligonucleotides 1 and 3 are annealed and oligonucleotides 2 and 4 are annealed to produce two duplexes. The resulting duplexes are ligated using the complementary overhangs at the right end of the 1/3 duplex and the left end of the 2/4 duplex The resulting fragment has the structure:

EcoRI site-PEP1-BglII site-flexible linker-PEP2-EcoRI

It is inserted into the EcoRI site of pTIN500. (FIG. 3(b)).

Using the same standard approaches a person skilled in the art can make various combinations of peptides. For example:

(PEP1-linker-PEP1)n
(PEP2-linker-PEP2)n
(PEP1-linker-PEP2)n
(PEP2-linker-PEP1)n Where n can be any number of repeats.

In addition to the constructions described it would be possible for anyone skilled in molecular biology and possessing a knowledge of the established rules for achieving effective gene expression in eukaryotic cells to make improvements and generate different combinations of coding sequences according to the principles outlined. For example the codon usage could be optimised as described by Haas et al (1996), the sequences could be linked with any other therapeutic gene, or the repetition of sequences could be altered.

c) Expression of peptides in a poly-cistronic transcription unit.

Multiple copies of the peptides may be expressed in a single vector by using an internal ribosome entry site (IRES). In the present example the 5' non-coding region of human immunoglobulin heavy-chain binding protein (BiP) (Macejak and Sarnow 1991) is used. Other IRES could be used to achieve the same result for example the 5' leader of picornavirus RNAs (Pelletier and Sonnenberg 1988; Molla et al 1992). The use of multiple IRES elements in a retroviral vector has been described (Morgan et al 1992) and use of these elements in retroviral vectors is described in WO 94/24870.

The BiP IRES is isolated from plasmid pSVA-Cat-BiP-Luc (Macejak and Samow 1991) as a 210 bp fragment (Sequence 5NCHUBIP; SEQ ID No:12) using the PCR primers indicated below and on FIG. 4.

PCR primer 1:
5'GGCAGATCTTCGACGCCGGCC [SEQ ID NO: 13]
PCR primer 2:
5'GGCCGGAATTCCCTCGAGAGAGGATCCT-TGGGCAGCAGC [SEQ ID NO: 14]

The configuration of the BiPIRES fragment is:

BglII-IRES-BamHI-XhoI-EcoRI

The EcoRI to BglII fragment of Pep1 (SEQ ID NO: 5) is ligated to the BglII to EcoRI fragment of Pep2 (SEQ ID NO: 6). The resulting fragment is inserted into the Eco RI site of an intermediate cloning vector pGEM-9Z (Cat.No. P2391, Promega). The intermediate molecule is digested with BglII and ligated to the BiPIRES fragment that is digested with BglII and BamHI. The intermediate cloning molecule is then digested with EcoRI to release an EcoRI fragment comprising Pep1-IRES-Pep2 which is ligated into the EcoRI site of pTIN500 (FIG. 3(c)).

d) Expression of mutant p17 (p17M) proteins

EcoRI fragments encoding p17M are prepared from the respective mutated proviral clones described in Table 1, by PCR using the following primers:

Primer 1:
5'GGCCGAATTCGTCGACACCATGGGTGCGAGCG [SEQ ID NO:15]
Primer 2:
5'CCGGAATTCACTCGAGATCTG-TAATTTTGGCTGACC [SEQ ID NO:16]

The resulting fragment has the structure:

EcoRI-SalI-p17-BglII-XhoI-EcoRI.

Figure 5:
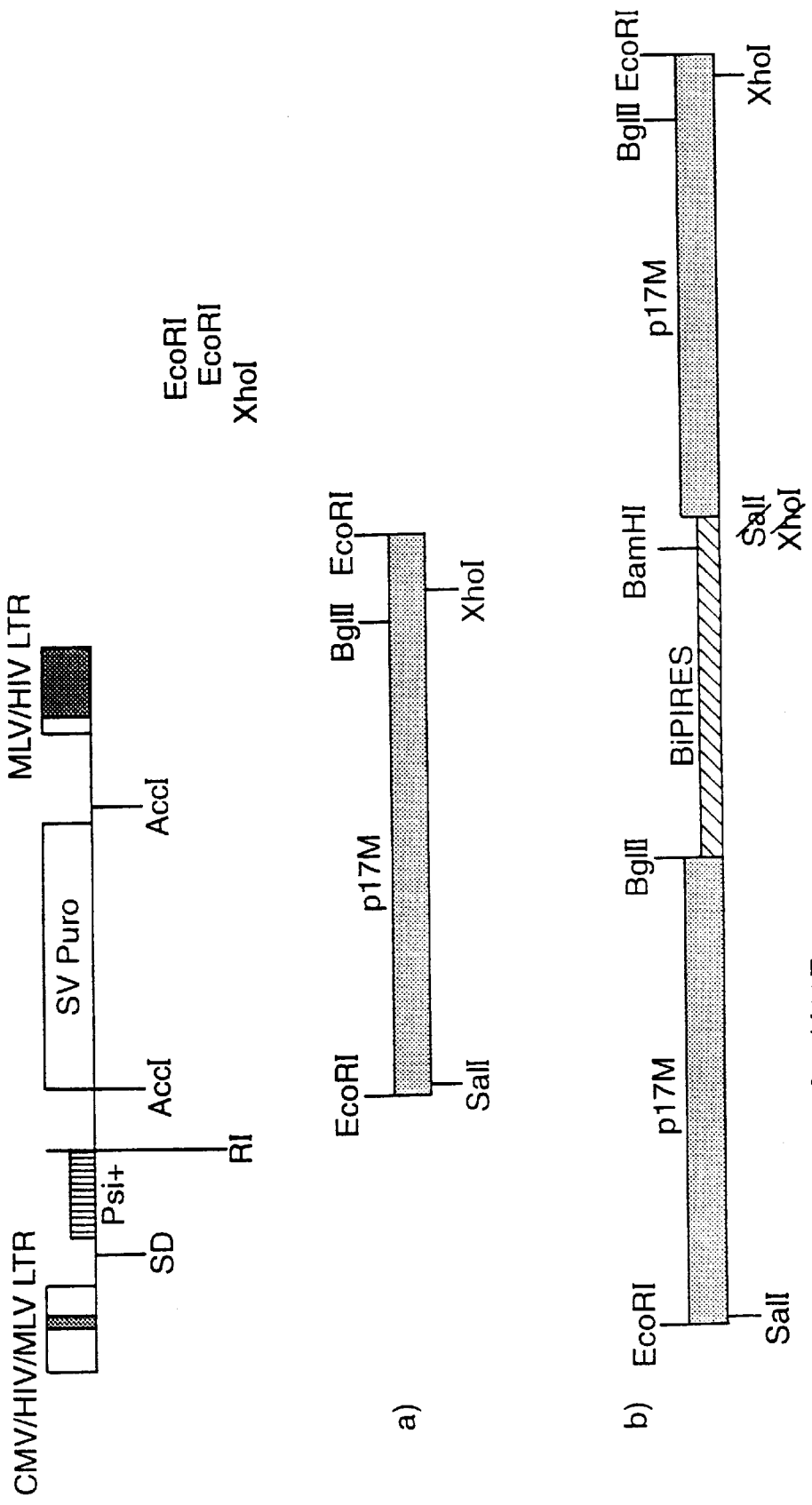
FIG. 5 shows an HIV-based retroviral vector encoding (a) a single mutant p17; and (b) two mutant p17 polypeptides, as described herein.

It is inserted into the EcoRI site in pTIN500 to produce pTIN500p17M (FIG. 5(a)).

e) Expression of multiple p17 mutant proteins pTIN500 p 17M is digested with BglII and XhoI and ligated with the BiPIRES fragment (SEQ ID No. 9) which is digested with BglII and XhoI. The resulting vector pTIN500 p17MBiP is digested with XhoI and ligated with a second p17M sequence digested with SalI and XhoI. This creates a retroviral vector capable of expressing two p17M sequences (FIG. 5(b)). These could be the same or different sequences.

Example 2

The analysis of inhibitory peptides and proteins
Retroviral vector stocks are produced by transient transfection of 293T cells according to our previously published protocol (Soneoka et al. 1995). MLV packaging components are provided in trans on two plasmid 20 components—a gag-pol expression plasmid (pHIT60) and an amphotropic or ecotropic envelope construct (pHIT456 or pHIT123 respectively). The vector genome component is either a standard MLV vector (pHIT111) or one of the vectors outlined in FIGS. 3 and 4. Virus stocks generated 48 hours after transfection are used to infect U937 cells. Two days later, the transduced cells and a control U937 population are challenged with HIV-1. Viral spread is monitored by assaying the supernatant every three days for RT activity. The rate of viral replication is delayed in the U937 population relative to the control cells, due to the induction of the anti-viral p17 peptides and proteins in those cells.

REFERENCES

Aumally et al 1990. FEBS Lett. 262: 82.

Baltimore, D. (1988). Intracellular immunization. Nature 335:395–396.

Bukrinskaya, A. G., Ghorpada, N. K., Heinzinger, N. K. et al (1996). Phosphorylation dependent human immunodeficiency virus type 1 infection and nuclear targeting of viral DNA. Proc. Natl. Acad. Sci. 93: 367.

Burinsky, M. I., Haggerty, S., Dempsey, M. P., Sharova, N. et al (1993). Nature 365: 666–669.

Cannon, P. M., Kim, N., Kingsman, S. M. and Kingsman, A. J. (1996). Murine Leukaemia virus-based Tat inducible long terminal repeat replacement vectors: a new system for anti-human immunodeficiency virus gene therapy. J. Virol. 70: 8234.

Cannon, P. M., Wilson, W., Byles, E., Kingsman, S. M., and Kingsman, A. J. (1994). J.Virol. 68: 4768–4775.

Dekker et al 1993, Nature, 362: 852

Gelderblom, H. R. (1991). Assembly and morphogenesis of HIV: potential effect of structure on viral function. AIDS 5: 617.

Haas et al 1996. (In Parkinsons patent)

Herskowitz (1987). Nature 329: 219.

Hill, C. P., Worthylake, D., Bancroft, D. P. et al (1996). Crystal structures of the trimeric HIV-1 matrix protein: implications for membrane association and assembly. Proc. Natl. Acad. Sci. 93: 3099.

Hofmann,B., Nishanian, P., Michael, N. et al (1994). HIV Gag p17 protein impairs proliferation of normal lymphocytes in vitro. AIDS 8: 1016.

Karacostas, V., Wolff, E. J., Nagashima, K et al (1993). Over expression of the HIV-1 Gag-Pol poly-protein results in intracellular activation of HIV-1 protease and inhibition of assembly and budding of virus-like particles. Virology, 193: 661

Kim, S., R. Bym, J. E. Groopman, and D. Baltimore. (1989). Temporal aspects of DNA and RNA synthesis during human immunodeficiency virus infection:, evidence for differential gene expression. J. Virol. 63:3708–3713.

Kimpton, J., Emerman, M. (1992). J. Virol. 66: 2232–2239.

Lee, P. P. and Linial, M. L.(1995). Inhibition of wild type HIV-1 virus production by a matrix deficient gag mutant. Virology, 208: 808.

Lehrman, S. (1994). Nature 371: 192.

Lori, F., Lisziewicz, J., Smythe, J et al (1994). Rapid protection against human immunodeficiency virus type 1 replication mediated by high efficiency non-retroviral delivery of genes interfering with HIV-1 tat and gag. Gene Therapy, 1: 27.

Luban, j., Bossolt, E. K., Franke, G. et al (1993). Human immunodeficiency virus type 1 Gag protein binds to cyclophilins A and B. Cell, 73: 1067.

Macejek, D. G. and Sarnow, D. G. (1991). Internal initiation of translation mediated by the 5' leader of a cellular RNA. Nature, 353: 90.

Massiah, M. A., M. R. Starich, C. Paschall, M. F. Summers, A. M. Christensen, and W. I. Sundquist. 1994. Three-dimensional structure of the human immunodeficiency virus type 1 matrix protein. J. Mol. Biol. 244:198–223.

Matthews, S., P. Barlow, J. Boyd, G. Barton, R. Russell, H. Mills, M. Cunningham, N. Meyers, N. Burns, N. Clark, S. Kingsman, A. Kingsman, and I Campbell. 1994. Structural similarity between the p17 matrix protein of HIV-1 and interferon-g. Nature 370:666–668.

Miele, G. and Lever, A. (1996). Expression of mutant and wild type gag proteins for gene therapy in HIV-1 infection. Gene Therapy, 3: 357.

Modrow, S., Kattenback, B., Von Poblotzki et al (1994) The Gag proteins of human immunodeficiency virus type 1: mechanisms of virus assembly and possibilities for interference. Med. Microbiol. and Immunol. 183: 177.

Molla, A., Jang, S. K., Paul, A. et al (1992). Cardioviral internal ribosomal entry site is functional in a genetically engineered dicistronic poliovirus.

Morgan, R. A., Couture, L., Elroy-Stein, O. et al (1992) Retroviral vectors containing putative internal ribosome entry sites: development of a polycistronic gene transfer system and applications to human gene therapy. Nucl. Acids Res. 20: 1293.

Neidrig, M., Pauli,J, Marz, H et al (1994). Inhibition of infectious human Immunodeficiency virus type I particle formation by Gag protein derived peptides. J. Genetic Virol. 67: 7229.

Nermut, M. V., Hockley, D. J.,et al (1994). Fullerene like organisation of HIV-1 Gag protein shell in virus-like particles produced by recombinant baculovirus. Virology 198:288.

Pelletier, J and Sonnenberg, N. (1988). Nature 334: 320

Reicin, A. S., S. Paik, R. D. Berkowitz, J. Luban, I. Lowy, and S. P. Goff. 1995. Linker insertion mutations in the human immunodeficiency virus type 1 gag gene: effects on virion particle assembly, release, and infectivity. J. Virol. 69:642–650.

Smythe, J., Sun, D., Thomson, M. et al (1994) Proc. Natl.Acad. Sci.

Somia et al (1993) PNAS 90: 7889

Soneoka, Y., Cannon, P., Ramsdale, E. et al (1995). A transient three plasmid expression system for the production of high titre retroviral vectors. Nucleic Acids Res. 23: 628.

Trono, D., Feinberg, M. and Baltimore, D. Gag mutants can dominantly interfere with the replication of wild type virus. Cell, 59: 113.

Wickham et al Gene Therapy, 1995. 2: 750.

Wiederrecht et al (1988). Cell, 54: 841.

Yu, G., Shen, F. S., Sturch, S. et al (1995). Regulation of HIV-1 Gag protein sub cellular targeting by protein kinase C. J. Biol. Chem., 270: 4792.

Yu, M., E. Poeschla and F. Wong-Staal. (1994). Progress towards gene therapy for HIV infection. Gene Therapy 1:13–26.

Yu, X., Yu Q. C., Lee, T. H. (1992). The C terminus of human immunodeficiency virus type 1 matrix protein is involved in the early steps of the virus life cycle. J. Virol. 66: 5667.

Yuan, X., Yu, X., Lee, T.-H. and Essex, M. (1993). J. Virol. 67: 6387–6394.

Zhao, Y., Jones, I. M., Hockley, D. J. et al (1994). Complementation of human immunodeficiency virus (HIV-1) gag particle formation.

Zhou, W., Parent, L. J., Wills, J. W. and Resh, M. D. (1994). J. Virol. 68: 2556–2569.

What is claimed is:

1. A recombinant p17 protein which is incapable of functioning as the natural protein as a result of substitution of amino acid residue A45.

2. A recombinant p17 protein which is incapable of functioning as the natural protein as a result of substitution of amino acid residues R39 or R43.

3. A recombinant p17 protein according to claims 1 or 2, which is a natural or engineered variant of the HIV protein, said variant containing one or more conservative amino acid substitutions.

4. A composition comprising a peptide of claims 1 or 2 with a carrier or diluent.

* * * * *